United States Patent [19]
Kiessling et al.

[11] Patent Number: 5,587,442
[45] Date of Patent: Dec. 24, 1996

[54] POLYGLYCOMERS

[76] Inventors: Laura L. Kiessling, 2320 Lakeland Ave., Madison, Wis. 53704; David D. Manning, 1906 Pike Dr., Apt. 1, Madison, Wis. 53713; Kathleen H. Mortell, 202 G Eagle Heights, Madison, Wis. 53705

[21] Appl. No.: 363,503

[22] Filed: Dec. 23, 1994

[51] Int. Cl.$^6$ ............................ A01N 43/04; A61K 31/70
[52] U.S. Cl. .................. 526/238.2; 526/238.23; 514/23
[58] Field of Search ............................ 526/238.2, 238.23; 514/23

[56] References Cited

U.S. PATENT DOCUMENTS

| | | | |
|---|---|---|---|
| 4,883,851 | 11/1989 | Grubbs et al. | 526/268 |
| 5,100,972 | 3/1992 | Sivavec et al. | 525/391 |

*Primary Examiner*—Nathan M. Nutter

[57] ABSTRACT

A polyglycomer is disclosed of the following formula:

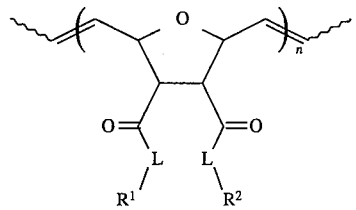

wherein L is a linker selected from the group of —O—$(CH_2)_m$—, —NH—$(CH_2)_m$—, —O—$(CH_2)_m$—X—, and —NH—$(CH_2)_m$—X—, wherein X=S or O and m is 2–10, wherein $R^1$ and $R^2$ are selected from the group consisting of saccharide moieties, and wherein n is between 1 and 2000. A method of creating a polyglycomer is also disclosed.

16 Claims, 11 Drawing Sheets

1-C-Allyl-2,3,4,6-TETRA-O-
TRIETHYLSILYL-α-D-GLUCOPYRANOSIDE.

GLUCOSIDE ALCOHOL 1.

PRECURSOR TO 3

GLUCOSE-SUBSTITUTED MONOMER 3

GLUCOSE POLYGLYCOMER 4

FUCOSE POLYGLYCOMER 5

8: $R^1$ = SO$_3$Na   10: $R^1$ = SO$_3$Na
   $R^2$ = H            $R^2$ = SO$_3$Na

9: $R^1$ = H
   $R^2$ = SO$_3$Na

—O—Pr WILL BE SUBSTITUTED BY L

POLYGLYCOMERS

This invention was made with United States government support awarded by NIH Grant #CM49975 and NSF Grant No. CHE-9357093. The United States Government has certain rights in this invention.

FIELD OF THE INVENTION

In general, the field of the present invention is carbohydrate-substituted polymers. Specifically, the field of the present invention is saccharide-substituted polymers formed from 7-oxanorbornenes through aqueous ring-opening metathesis polymerization.

BACKGROUND

Intercellular recognition events are fundamental to many biological processes including fertilization, development, and the mounting of an immune response. Although little is known of the molecular mechanisms underlying cell recognition and adhesion, cell surface oligosaccharides have been implicated as key participants in many of these events. (Hughes, *Curr. Opin. Struct. Biol.* 2:687–92, 1992; Drickamer, et al., *Annu. Rev. Cell Biol.* 9:237–64, 1993; Bock, et al., "Carbohydrate Recognition in Cellular Function," John Wiley & Sons Ltd: Chichester, UK, 1989; Vol. 145.) Carbohydrate receptors often bind weakly to target saccharide ligands in solution (i.e., with $K_a=10^3-10^4$ M). (Lee, *Fed. Proc. Fed. Am. Soc. Exp. Biol.* 6:3193–3200, 1992.) FIG. 1 describes the lectin concanavalin A (Con A) binding to multiple mannose residues on the surface of erythrocytes.

Thus, nature takes advantage of multivalent carbohydrate-protein interactions to enhance the strength of cell surface binding. (Karlsson, *Annu. Rev. Biochem.* 58:309–350, 1989; Goldhar, *Methods Enzymol.* 236:211–231, 1994.) Molecules that can mimic the polyvalent display of oligosaccharides presented by a cell surface should be more effective than monovalent ligands at modulating intercellular interactions (DeFrees, et al., *J. Am. Chem. Soc.* 115:7549–7550, 1993; Matrosovich, et al., *FEBS Lett.* 272:209–212, 1990; Spaltenstein, et al., *J. Am. Chem. Soc.* 113:686–687, 1991; Roy, et al., *J. Chem. Soc., Chem. Commun.* pp. 1869–1872, 1993; Kingery-Wood, et al., *J. Am. Chem. Soc.* 114:7303–5, 1992; Spevak, et al., *J. Am. Chem. Soc.* 115:1146–1147, 1993; Glick, et al., *J. Biol. Chem.* 266:23660–23669, 1991; Sabesan, et al., *J. Am. Chem. Soc.* 114:8363–75, 1992).

Three general approaches used for the synthesis of multivalent carbohydrate derivatives are (1) attachment of carbohydrate residues to an acrylamide polymer backbone (Matrosovich, et al., *FEBS Lett.* 272:209–212, 1990; Spaltenstein, et al., *J. Am. Chem. Soc.* 113:686–687, 1991; Roy, et al., *J. Chem. Soc., Chem. Commun.* pp. 1611–13, 1992), (2) incorporation of carbohydrate bearing lipids into liposomes (Kingery-Wood, et al., *J. Am. Chem. Soc.* 114:7303–5, 1992; Spevak, et al., *J. Am. Chem. Soc.* 115:1146–1147, 1993) and (3) conjugation of carbohydrate groups to a protein (Welply, et al., *Glycobiology* 4:259–265, 1994). With these methods, it is difficult to control the size of the multivalent ligand and the density of carbohydrate substituents.

We sought an alternative polymerization method that would have the potential for greater control of polymer size, structure, and the density of carbohydrate substituents. In addition, we wanted a flexible strategy that would allow the production of copolymers to synthesize materials for selective immobilization of different cell types. Finally, the chosen polymerization reaction should tolerate a highly polar monomer bearing unprotected sugars.

SUMMARY OF THE INVENTION

The present invention is a compound of the formula:

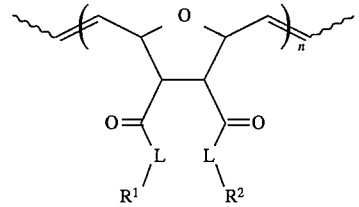

wherein L is a linker selected from the group of —O—$(CH_2)_m$—, —NH—$(CH_2)_m$—, —O—$(CH_2)_m$—X— and —NH—$(CH_2)_m$—X— moieties, wherein X=O or S and m is 2–10; and wherein $R^1$ and $R^2$ are selected from the group consisting of saccharide moieties, and wherein n is between 1 and 2000. We have named such a compound a "polyglycomer." Preferably, L=—O—$CH_2$—$CH_2$— and is attached to $C_1$ position of the reducing end of the saccharide moiety.

In a preferred embodiment of the present invention, $R^1$ and $R^2$ are selected from the group of monosaccharides, disaccharides, trisaccharides and oligosaccharides.

In an especially preferred embodiment of the present invention n is approximately 1800. In another preferred version of the present invention n is less than 20. In another preferred embodiment of the invention, n is between 1000 and 2000.

The present invention is also a polyglycomer of the formula:

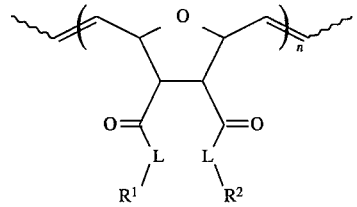

wherein L is a linker selected from the group of —O—$(CH_2)_m$—, —NH—$(CH_2)_m$—, —O—$(CH_2)_m$—X— and —NH—$(CH_2)_m$—X— wherein X=O or S and m is 2–10; and wherein $R^1$ and $R^2$ are selected from the group consisting of moieties of the formula:

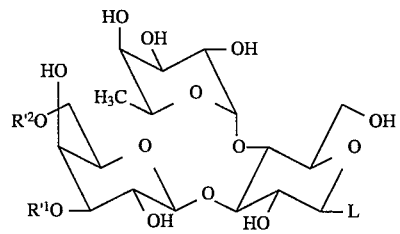

wherein $R'^1$=$SO_3Na$ and $R'^2$=H; or $R'^1$=$SO_3Na$ and $R'^2$=$SO_3Na$; or $R'^1$=H and $R'^2$=$SO_3Na$, and wherein n is between and 1 and 2000.

The present invention is also a compound of the formula

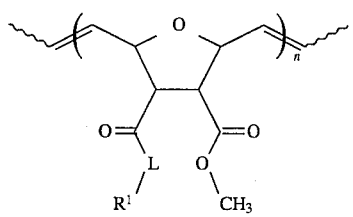

wherein L is a linker selected from the group of —O—(CH$_2$)$_m$—, —NH—(CH$_2$)$_m$—, —O—(CH$_2$)$_m$—X— and —NH—(CH$_2$)$_m$—X— moieties, wherein X=O or S and m is 2–10; and wherein R$^1$ is selected from the group of saccharide moieties, and n is between 1 and 2000.

The present invention is also a compound of the formula

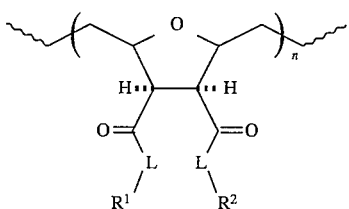

wherein L is a linker selected from the group of —O—(CH$_2$)$_m$—, —NH—(CH$_2$)$_m$—, —O—(CH$_2$)$_m$—X— and —NH—(CH$_2$)$_m$—X— moieties, wherein X=O or S and m is 2–10; and wherein R$^1$ and R$^2$ are selected from the group of saccharide moieties and wherein n is between 1 and 2000.

The present invention is also a method of treating inflammation comprising applying an effective amount of the polyglycomer described above to inflamed tissue.

The present invention is also a method of creating a polyglycomer comprising the steps of attaching at least one saccharide group to 7-oxanorbornene via a C-glycoside linkage and treating the product of the first step with ruthenium trichloride, wherein a polyglycomer is created. In a preferred form of this method, the ruthenium trichloride treatment is in a aqueous environment at 55° C.

It is an object of the present invention to create a polymer with multiple carbohydrate ligands.

It is another object of the present invention to create a polymer with carbohydrate ligands that comprise 1–4 carbohydrate residues.

It is another object of the present invention to create a selectin-targeted ligand.

It is another object of the present invention to provide an anti-inflammatory treatment method using the selectin-targeted ligand.

It is another object of the present invention to create a polyglycomer with a molecular weight of approximately 10$^6$.

It is another object of the present invention to provide a Con-A-targeted ligand.

It is an advantage of the present invention that a multivalent carbohydrate polymer is provided with means to control the size of the multivalent ligand, the density of the carbohydrate substituents, and the size of the polymer.

Other objects, advantages and features of the present invention will become apparent upon study of the specification, drawings and claims.

DESCRIPTION OF THE DRAWINGS

FIG. 3A depicts 1-C-allyl-2,3,4,6-tetra-0-triethylsilyl-α-D-glucopyranoside; FIG. 3B depicts glucoside alcohol 1; FIG. 3C depicts the precursor to 3; FIG. 3D depicts glucose-substituted monomer 3; FIG. 3E depicts glucose-polyglycomer 4; and FIG. 3F depicts fucose-polyglycomer 5.

DESCRIPTION OF THE INVENTION

Our desire to explore the chelate effect and to design molecules to regulate cell-cell interactions prompted us to investigate the aqueous ring-opening metathesis polymerization (ROMP, described in Novak, et al., *J. Am. Chem. Soc.* 110:7542–43, 1988; Nguyen, et al., *J. Am. Chem. Soc.* 114:3974–3975, 1992; and Nguyen, et al., *J. Am. Chem. Soc.* 115:9858–9859, 1993) for the synthesis of carbohydrate substituted materials. These have resulted in the synthesis of a new class of carbohydrate modified polymers which we call "polyglycomers." These polyvalent materials have unique biological properties relative to monomeric ligands. For example, we show below in the Examples that glucose-derivatized polyglycomers and mannose-derivatized polyglycomers act as potent inhibitors of concanavalin A (Con A) induced cell agglutination.

1. Ring-Opening Metathesis Polymerization (ROMP)

a. In General

Several features of ROMP recommend it for the synthesis of bio-active polymers: (1) the polymerization can be effected in water (Novak, et al., *J. Am. Chem. Soc.* 110:7542–43; 1988; Nguyen, et al., *J. Am. Chem. Soc.*

114:3974–3975, 1992), (2) monomers with unprotected hydroxyl groups can be polymerized, (3) polymers can be end-capped with useful functionality using chain-transfer alkenes, and (4) ROMP can be used to synthesize block copolymers.

Figure 1:
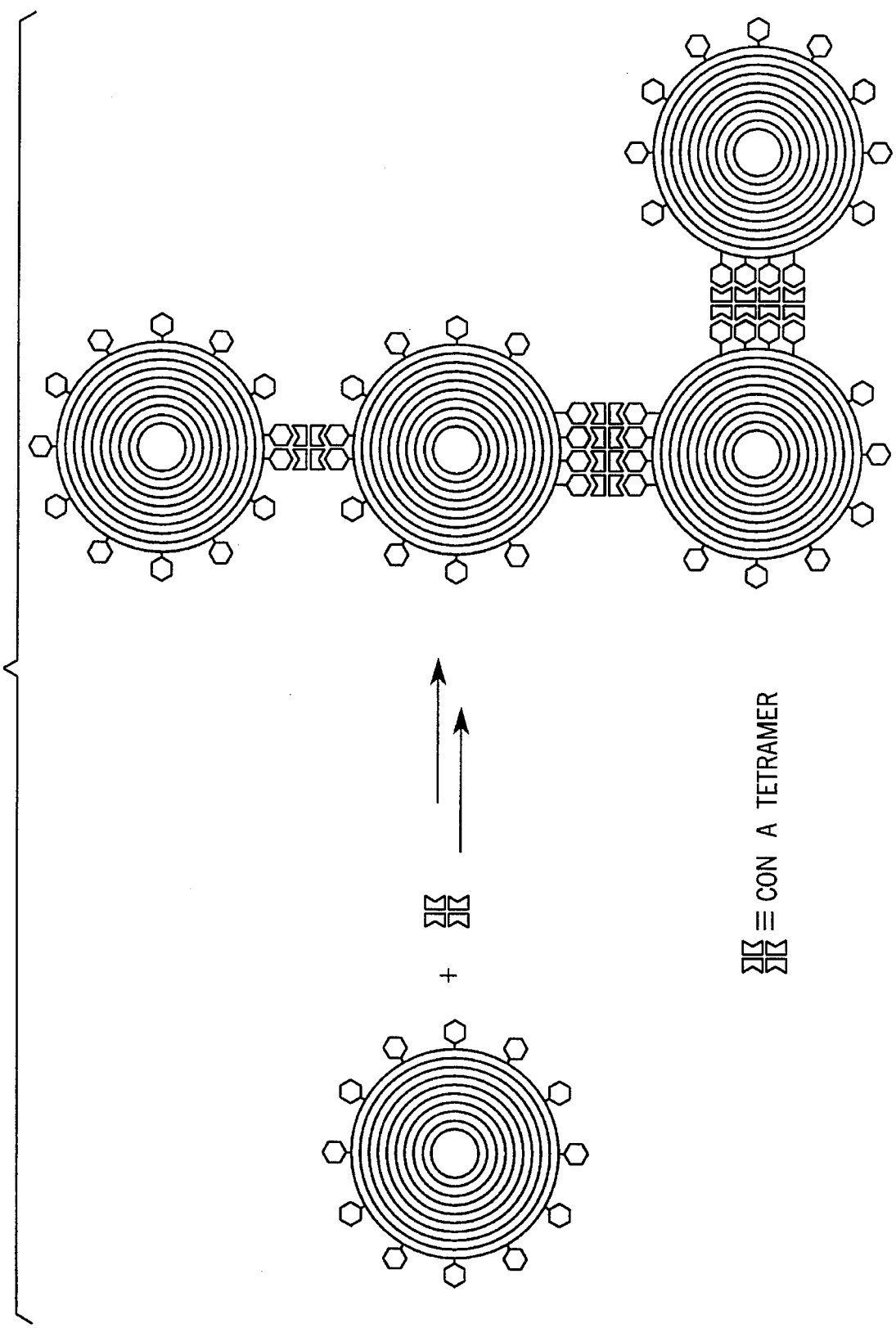
FIG. 1 is a schematic diagram of the binding of the Con tetramer to multiple terminal mannose residues on the surface of erythrocytes.
Figure 2:
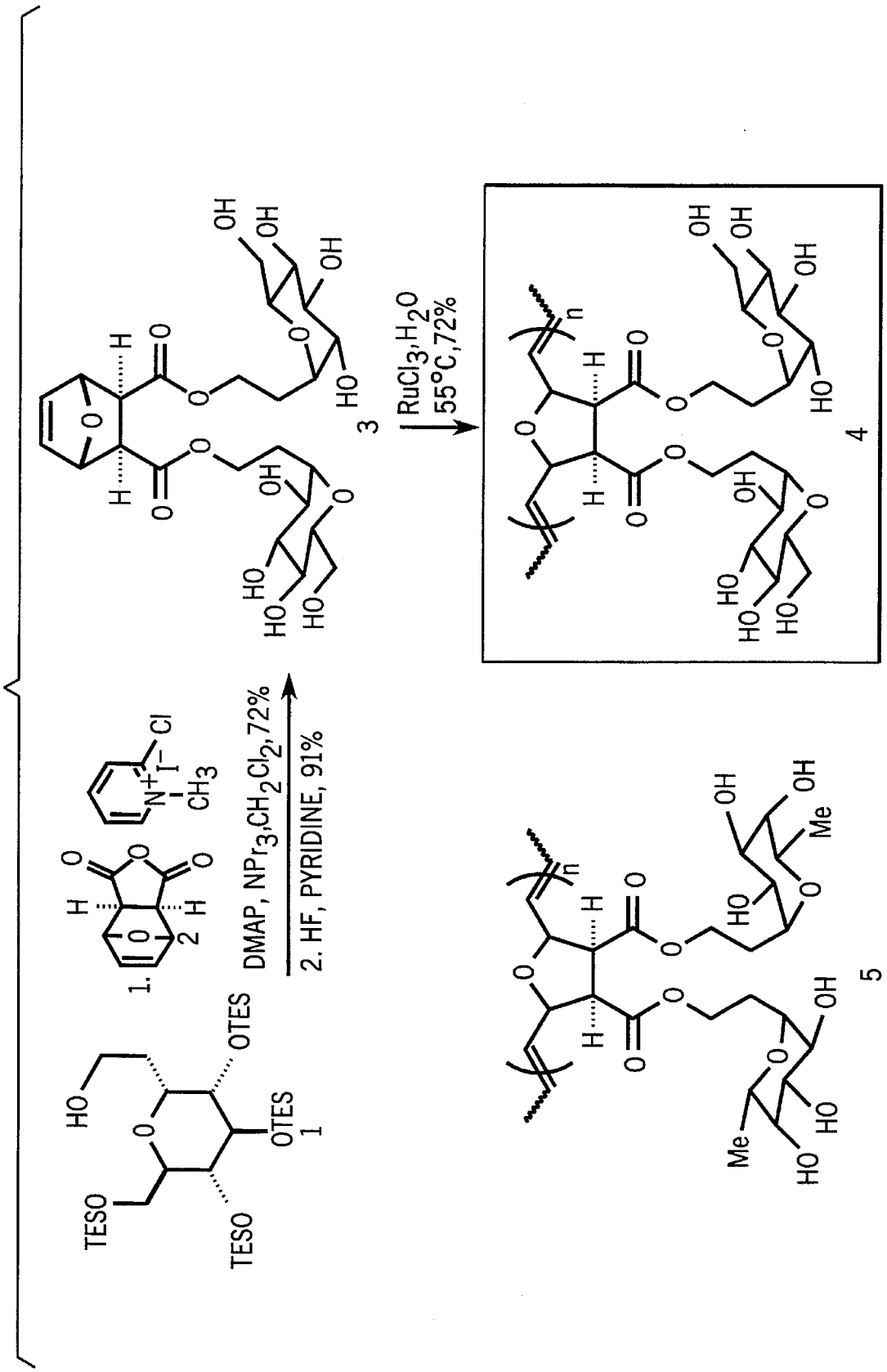
FIG. 2 is a schematic diagram of the synthesis of compounds 4 (glucose-derivatized polyglycomer) and 5 (fucose-derivatized polyglycomer).

We have demonstrated below in the Examples that ruthenium catalysts in aqueous solutions promote ROMP reactions of highly polar monomers such as glucose monomer 3. (FIG. 2, which describes one of our Examples, is a schematic diagram of the synthesis of a polymer from the glucose monomer 3. FIG. 3 describes the reaction products and intermediates that are involved in the synthesis of a glucose polyglycomer and fucose polyglycomer.) The application of ROMP to the synthesis of carbohydrate-substituted polymers offers new opportunities for the design of materials for the modulation of cell adhesion, immobilization of particular cell types, and study of multivalency in extracellular interactions. FIG. 3F depicts a typical polyglycomer of the present invention. The terminal groups of the molecule are not specified in FIG. 3F. With these catalysts, the terminal groups of the polymer are not defined (see, Breslow, D. S., *Prog. Polym. Sci.* 18:1141–95, 1993).

One advantage of the ROMP is that this reaction can be used to produce block copolymers. Therefore, one might first polymerize with one type of substituted monomer. Upon addition of a second monomer, a polymer with two types of functionality is generated. Specifically, a mannose-substituted monomer could be polymerized followed by a fucose-substituted monomer to afford a material that has mannose groups on half the structure and fucose groups on the other half. Because different cells possess receptors for different saccharide residues, they would therefore bind to different regions of the polymer. This could be a useful method for generating surfaces of cells located in defined areas.

b. Synthesis of Polyglycomers

Polyglycomers of the present invention are created by attaching at least one saccharide group to 7-oxanorbornene, preferably via a C-glycoside linkage, and treating the product of this step with ruthenium trichloride. The Examples below describe a preferable method of creating a polyglycomer. In brief, monomeric precursors are generated by attachment of a saccharide residue to 7-oxanorbornene systems via C-glyside linkers. Ruthenium catalyzed ROMP of the resulting alkenes provides polyglycomers.

When the saccharide is attached with a "C-glycoside linker", the "linker" element of the general formula described above is —O—$CH_2$—$CH_2$—. However, we envision that other linkers would be equally successful. For example, —O—$(CH_2)_m$—, —NH—$(CH_2)_m$—, —O—$(CH_2)_m$—X—, and —NH—$(CH_2)_m$—X— where X is either O or S and m=2–10. Toshima, et al., *Chem. Rev.* 93:1503–1531, 1993 and Giannis, et al., *Tetrahedron Lett.* 26[12]:1479–1482, 1985 describe the generation of linkers attached to saccharides. (These articles are incorporated by reference as if fully set forth below.)

The Examples below specifically describe the creation of a mannose, glucose and fucose polyglycomer. However, we envision that many different saccharide residues would be suitable for the present invention. By "saccharide" we mean any one of the class of simple carbohydrates or sugars. Both hexoses and pentoses are suitable, although hexoses are preferred. Preferably saccharides are monosaccharides; such as glucose, fucose, mannose and sialic acid; disaccharides, such as lactose; trisaccharides, such as 3-sulfo-Lewis a and 3-sulfo-Lewis x; and oligosaccharides, such as heparin. (By oligosaccharide, we mean a molecule with approximately 3 to 50 sugar residues.) The Examples below also describe an advantageous tetrasaccharide, a selectin ligand.

Our experiments describe below with glucose, mannose and fucose polyglycomers indicate that many other saccharide residues would be effective. A variety of saccharide residues can be attached to the 7-oxanorbornene skeleton, preferably at the $C_1$ position of the reducing end of the saccharide, and we have demonstrated that such densely functionalized molecules will undergo ROMP.

Saccharide molecules are frequently combined with other moieties. We mean for the term "saccharide" to include sugars with various substituents, such as sulfate and phosphate. For example, the Examples below describe a trisaccharide ligand with sulfated residues. These saccharides with modified residues are expected to undergo ROMP and included in our definition of saccharide.

The Example below begins with a triethylsilyl-protected allyl glucoside. If a saccharide other than glucose is desired, the beginning material would be the allyl-C-glycoside or the allyl-O-glycoside or the C- or O-glycoside containing alcohol or amino groups. These materials may be obtained by standard synthetic methods or purchased commercially. (See, e.g., Giannis, et al., *Tetrahedron Lett.* 26:1479–1482, 1985.)

The next step is the creation of an alcohol from the protected moiety. The Examples below describe a preferred method of dissolving the glucoside in a 1:2 mixture of $CH_2Cl_2$/MeOH and cooling to $-78°$ C. Ozone is bubbled through the solution for 6 minutes, until the solution is saturated with ozone. Sodium borohydride (0.6 g, 15 mmol) is added in one portion and the mixture is stirred at $-78°$ C. for 1 hour, then at $3°$ C. for 1 hour. The reaction is quenched with aqueous ammonium chloride (15 mL), and the mixture is stirred for 1 hour at $3°$ C. Diethyl ether (20 mL) is added; the aqueous layer is extracted with ether (3×15 mL), and the combined ether extracts are washed with brine, dried over $MgSO_4$, and evaporated. The crude product is purified by flash chromatography (5%–7% ethyl acetate/hexane) to afford a clear oil (0.88 g, 1.33 mmol). A typical yield is 91%.

The alcohol (preferably 0.62 g, 0.94 mmol, 2.5 eq.) is then co-distilled with toluene to remove water. 3,6-oxy-1,2,3,6 tetrahydrophthalic anhydride (0.062 g, 0.38 mmol, 1 eq.), 4-dimethylaminopyridine (DMAP, 0.018 g, 0.15 mmol, 0.4 eq.), and 2-chloro-1-methylpyridinium iodide (0.12 g, 0.45 mmol, 1.2 eq.) are added to the alcohol. The flask is filled with argon and $CH_2Cl_2$ (2.0 mL) is added, followed by tripropylamine (0.21 mL, 1.1 mmol, 3 eq.). After stirring at $22°$ C. overnight, the suspension has typically cleared to a yellow solution. The reaction is diluted with 20 mL of ether. The ether layer is washed with aqueous ammonium chloride (2×10 mL), and brine (2×10 mL), dried over $MgSO_4$, and evaporated. The residue is purified by flash chromatography (3% ether/toluene) to give a clear oil (0.42 g, 0.27 mmol). Of the excess alcohol added, typically 82% is recovered.

The TES-protected precursor to the monomer is azeotroped with toluene and dissolved in THF (7.5 mL). The resulting solution is cooled in an ice bath. To this solution, HF•pyridine (0.92 mL) is added dropwise. The resulting mixture is stirred at $0°$ C. for 1.25 hours. The reaction mixture is then concentrated under reduced pressure. Methanol (5 mL) is added to the residue, and solvent is removed under reduced pressure. The residue is purified by flash chromatography (1:4:5 water/methanol/isopropanol eluent) to afford a White solid.

To a flask containing the derivatized 7-oxanorbornene and $RuCl_3 \cdot H_2O$ (2.0 mg, 9.6 μmol) under $N_2$ is added degassed water. The resulting black solution is heated at 55°–60° C. After 18 hours, a brownish-green gel is obtained, which is washed with acetone (2 mL) and methanol (2 mL) to afford a discolored solid. The solid is dissolved in water (10 mL), concentrated to 2 mL, and precipitated by the addition of methanol (10 mL). The supernatant liquid is decanted and the white precipitate is washed with methanol (2×1 mL). Excess solvent is evaporated under reduced pressure to afford a white solid (0.094 g, 72%). The solid is stable at room temperature for at least 5 months. The compound is hygroscopic, so it should be stored under a dry atmosphere, e.g. $N_2$ or argon.

c. Modifications i. Attachment of Two Different Residues

As described above, removal of the triethylsilyl protecting groups generated the polymer precursor 3 in FIG. 3. This route provides rapid access to monomers bearing two identical carbohydrate residues. To attach two different residues, a sequential coupling procedure can be used.

The following is a description of a preferred sequential coupling procedure: One equivalent of the glycoside alcohol is reacted with 3,6-oxy-1,2,3,6 tetrahydrophthalic anhydride (1 eq.), 4-dimethylaminopyridine (DMAP) (0.15 eq., catalytic) and triethylamine (2 eq.) in $CH_2Cl_2$ under $N_2$. The reaction is complete after 2 hours at room temperature. The product is purified by flash chromatography to yield a white solid (93%). To a flask containing the resulting monoacid/monoglycoside (1 eq.) is added 2-chloro-1-methylpyridinium iodide (1.2 eq.) and DMAP (0.15 eq.) A solution of the glycoside alcohol (1.1 eq.) in dry toluene (0.2M) is added, followed by tripropylamine (2.5 eq.), and the mixture is stirred under $N_2$ at 40° C. for 12 hours. The mixture is concentrated by rotary evaporation and purified by flash chromatography to give a clear oil (52%). This compound is deprotected and polymerized as described above.

ii. Functionalized Backbones

One advantage to using ROMP to generate bio-active compounds is that the product polymers possess a backbone that can be functionalized. Consequently, changes in the backbone may modulate the properties of the polymers. For example, reduction of the rigidifying alkene groups will afford polymers possessing increased conformational entropy, which may enhance or diminish the polymer's ability to interact with a protein such as Con A. In addition, the solubility properties of the reduced polymers may be changed. Another feature of the reduced polymers is that their NMR spectra will be simplified, allowing more complete analysis of the polymer structure.

Figure 9:
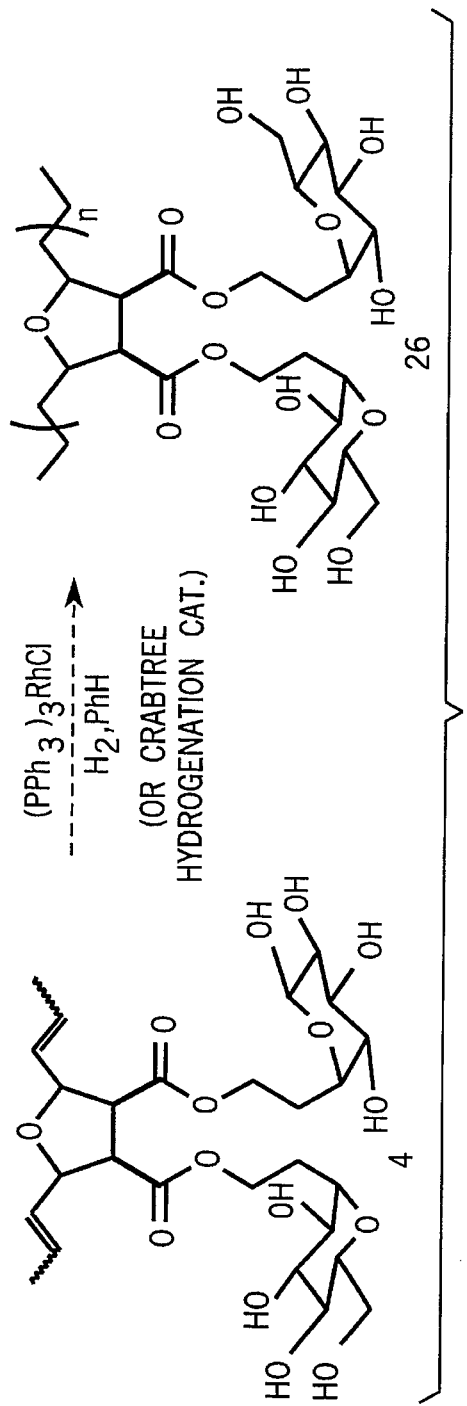
FIG. 9 describes proposed conditions for the reduction of the alkene backbone in glucose-polyglycomer 4.

To insure reduction of the backbone, a preferable method would be to employ either a Pd catalyst generated in situ, which has been used in the removal of benzyl protecting groups in peptides (Fields, et al., *Int. J. Peptide Res.* 35:161–214, 1990; Colombo, *J. Chem. Soc., Chem. Commun.* pp. 1012–1013, 1981), or homogeneous hydrogenation (Birch, et al., *Org. React.* 24:1–186, 1976; Brown, *Ang. Chem. Int. Ed. Eng.* 26:190–203, 1987). These methods will allow the reducing species to reach reactive sites within the polymer. These catalysts do not promote hydrogenolysis of allylic substituents, which would destroy the polymer scaffold. FIG. 9 describes preferable techniques for the reduction of an alkene backbone in glucose-polyglycomer 4.

iii. Synthesis of Mono-substituted Polyglycomers

To maximize the affinity of multivalent interactions, the proper spacing of individual recognition units is important. The density of saccharide residues displayed by a material can greatly affect its ability to function as a multivalent ligand (Sparks, et al., *J. Med. Chem.* 36:778–783, 1993;

Spevak, et al., *J. Am. Chem. Soc.* 115:1146–1147, 1993; Spaltenstein, et al., *The Jour. of Biol. Chem.* 269:1595–1598, 1994).

Figure 5:
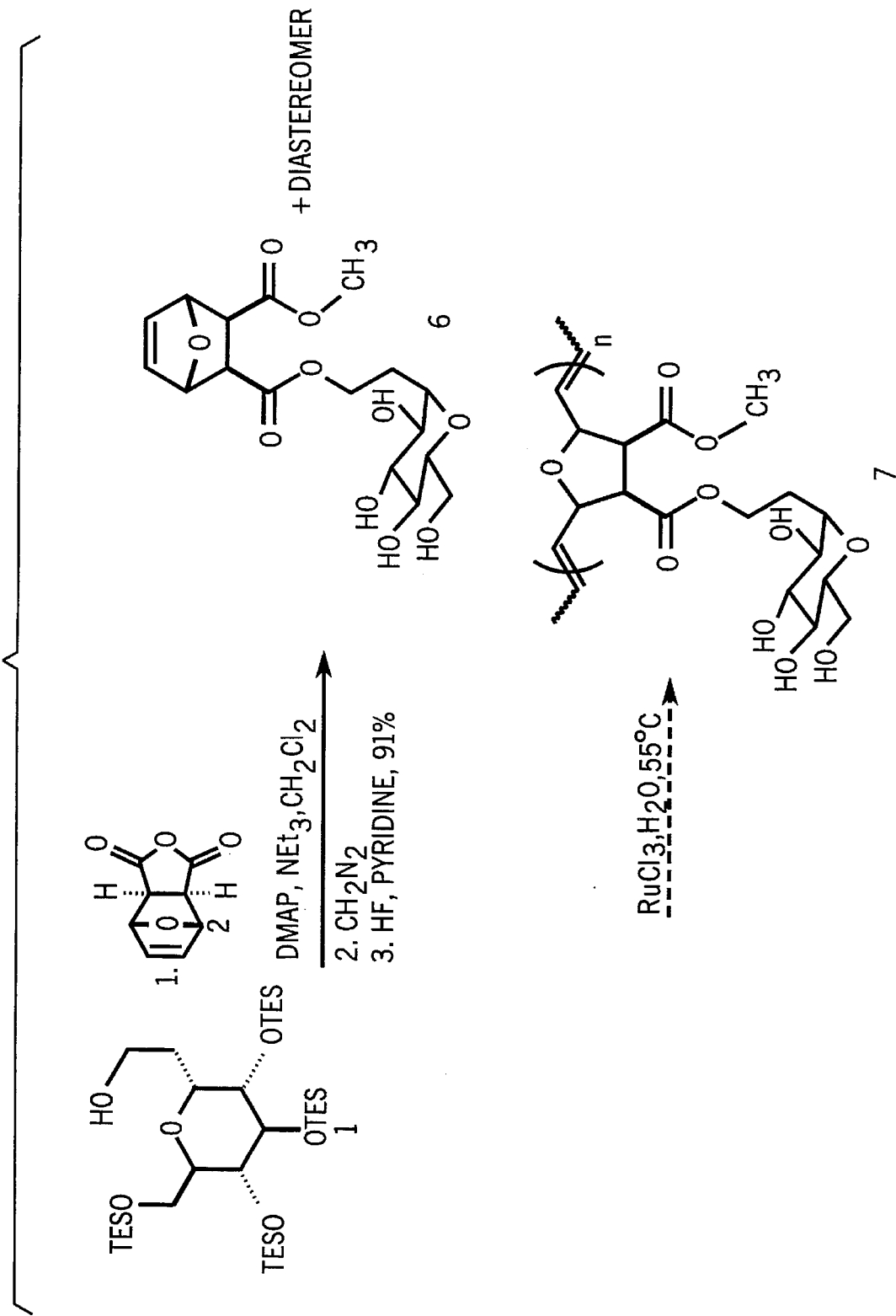
FIG. 5 is a schematic diagram of the synthesis of monosubstituted monomer 6 and a proposed conversion into polymer 7, which contains one saccharide residue per monomer unit.

The present invention includes oxanorbornene diastereomers 6 bearing a single saccharide group, for example the polyglycomer 7 depicted in FIG. 5. FIG. 5 describes preferred reaction conditions to create a oxanorbornene diastereomer bearing a single saccharide group and a polyglycomer created from that diastereomer. Simple opening of anhydride 2 with alcohol 1 affords a diastereomeric mixture of acid intermediates, which can be converted to the corresponding esters by treatment with diazomethane. The monomers may be polymerized using protocols described above.

iv. Addition of Chain-terminating Alkenes to Create Lower Molecular Weight Oligomers The synthesis of carbohydrate-bearing oligomers rather than polymers may afford nonimmunogenic substances which could be used as therapeutics. The method described above typically creates a polyglycomer wherein n=approximately 1800. However, polyglycomers of smaller sizes would be preferred for other applications. For example, polyglycomers of $n \leq 20$ would be especially preferred for their non-immunogenic property. In other applications, polyglycomers of n=1000 to 2000 would be preferred.

Figure 10:
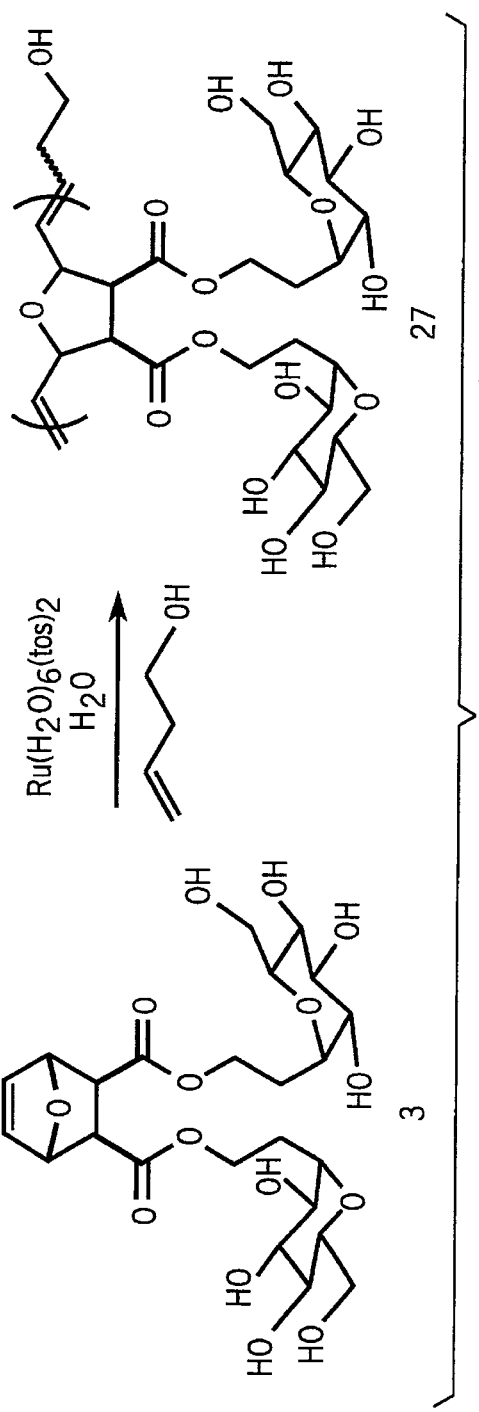
FIG. 10 describes the proposed application of a chain transfer agent to generate carbohydrate-substituted oligomers, such as 27.

FIG. 10 describes a typical proposed application of chain transfer agent to generate carbohydrate-substituted oligomers, such as 27. Oligomers created by this method are envisioned to be between 3 and 50 residues.

v. Creation of Tagged Polymers

Figure 11:
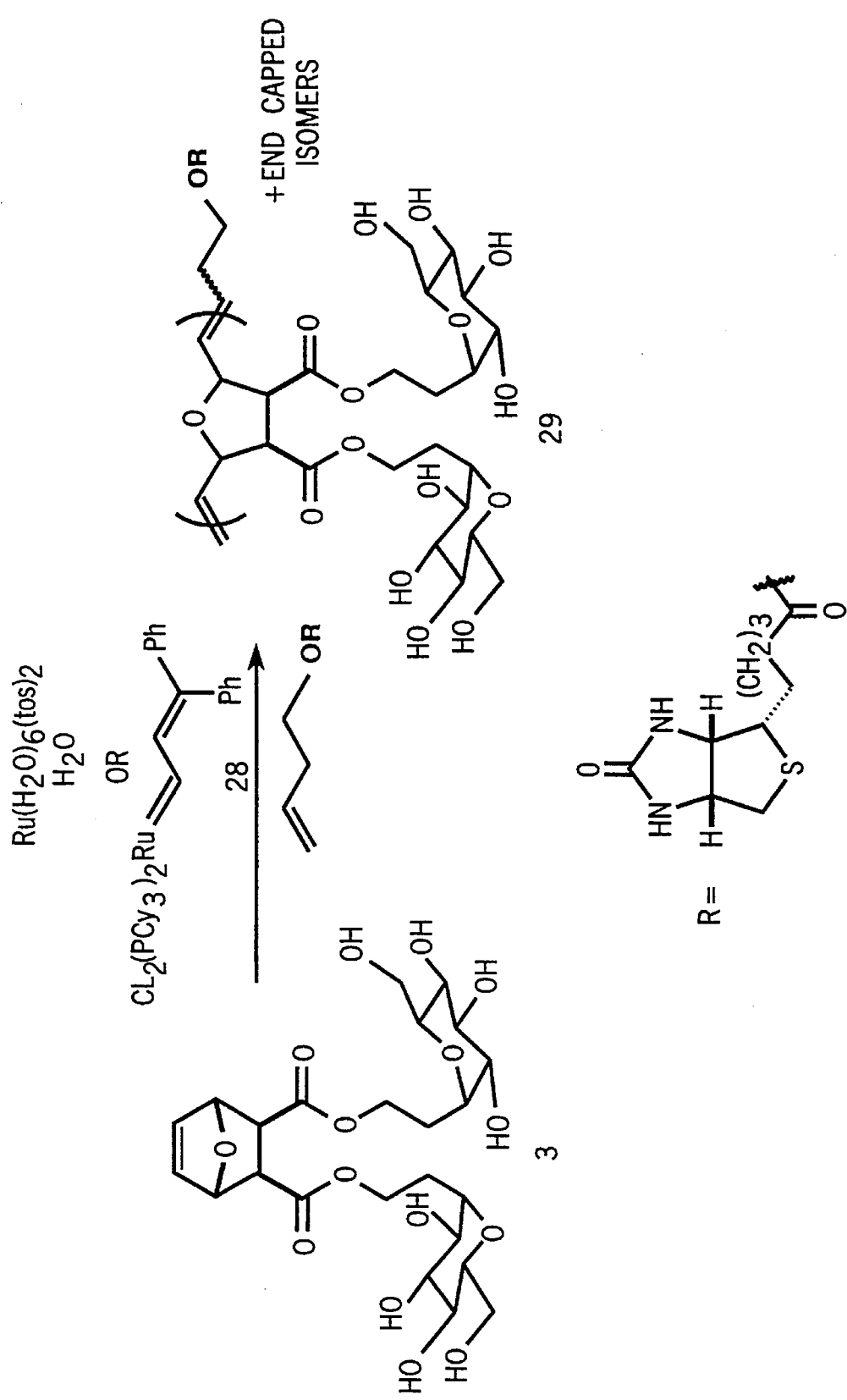
FIG. 11 describes the use of chain transfer agents carrying reporter groups to create polymers that are end-labelled with reporter groups, such as biotin.

Chain transfer agents can also be employed to end-label the polymers. FIG. 11 describes the use of chain transfer agents carrying reporter groups to lead to polymers that are end-labelled. Specifically, FIG. 11 describes the labelling of a polyglycomer with biotin. We envision that both ruthenium tosylate-derived catalyst or a defined ruthenium carbene catalyst 28 will be used. Although many end-labels would be suitable, biotin labelling is chosen as an example because of the wide-ranging potential uses. For example, the binding of the oligomers to cells could be monitored by taking advantage of biotin detection technology. In addition, the oligomers could be immobilized through the biotin-avidin interaction. Immobilized polyvalent ligands could be utilized to isolate receptors that bind carbohydrate determinants by multi-point attachment and to separate cells on the basis of their surface receptors.

The product of the polymerization reaction described in FIG. 11 may be loaded onto a biotin affinity column to selectively isolate the material that possesses the desired end-capping group and then subjected to gel filtration chromatography to determine the molecular weight.

2. Selectin-targeted Polyglycomers a. In General

Carbohydrate-protein interactions are implicated in inflammation (McEver, *Curr. Opin. In Immun.* 6:75–84, 1994; Bevilacqua, *Ann. Rev. Med.* 45:361, 1994).

In the early stages of inflammation, carbohydrateprotein interactions facilitate leukocyte rolling along the vascular endothelium (Von Andrian, et al., *Proc. Natl. Acad. Sci. USA* 88:7538–7542, 1991; Lawrence, et al., *The Jour. of Immun.* 151:6338–6346, 1993; Lawrence, et al., *Cell* 65:859–873, 1991). This event is mediated by carbohydrate binding proteins termed selectins, which use an N-terminal C-type lectin domain to bind surface oligosaccharide residues on opposing cells. With the identification of the carbohydrate binding properties of the selectins, oligosaccharides and their analogs emerged as new leads for the generation of anti-inflammatory agents. Additional impetus to develop anti-adhesive compounds is provided by the possibility that molecules that block selectin function could act as anti-cancer agents; cancer cells may use the selectin receptors in metastasis (Rice, et al., *Science* 246:1303–1306, 1989; Walz, et al., *Science* 250:1132–1135, 1990; Takada, et al., *Cancer Research* 53:354–361, 1993; Sawada, et al., *Int. J. Cancer* 57:901–907, 1994; Stone, et al., *Clin. Invest.* 92:804–813, 1993).

The discovery of the selectins highlights the potential for oligosaccharide-based therapeutics. Cell adhesion processes differ from receptor-ligand interactions in solution in that weak, multivalent interactions are often responsible for adhesion (Lee, *FASEB Jour.* 6:3193–3200, 1992). Progress has been slow in creating high affinity ligands for carbohydrate binding proteins by the traditional approach of modifying the structure of the monovalent ligand. However, imitation of the polyvalent binding environment can create better ligands for the modulation of cellular interactions. New methods for the synthesis of carbohydrate mimetics and multivalent carbohydrate bearing molecules are needed.

b. Role for Multivalency in Selectin Binding. The three known selectins, E-, P-, and L-, each participate in inflammation. The nomenclature designates the cell type on which each selectin was first identified: E-selectin is found on endothelial cells; P-selectin, on platelets and endothelial cells; and L-selectin, on leukocytes (Bevilacqua, et al., *Cell* 67:233, 1991). The display of each selectin on the cell surface occurs at different times during an acute inflammatory response. Specifically, L-selectin is a constitutive protein that is shed from the leukocyte surface upon activation; P-selectin is brought to the surface within minutes of endothelial cell activation and disappears within thirty minutes; protein synthesis of E-selectin occurs to display it within thirty minutes, and it remains on the cell surface for approximately 24 hours. The coordinated appearance and disappearance of the selectins is believed to direct the course of the inflammatory response.

Figure 4:
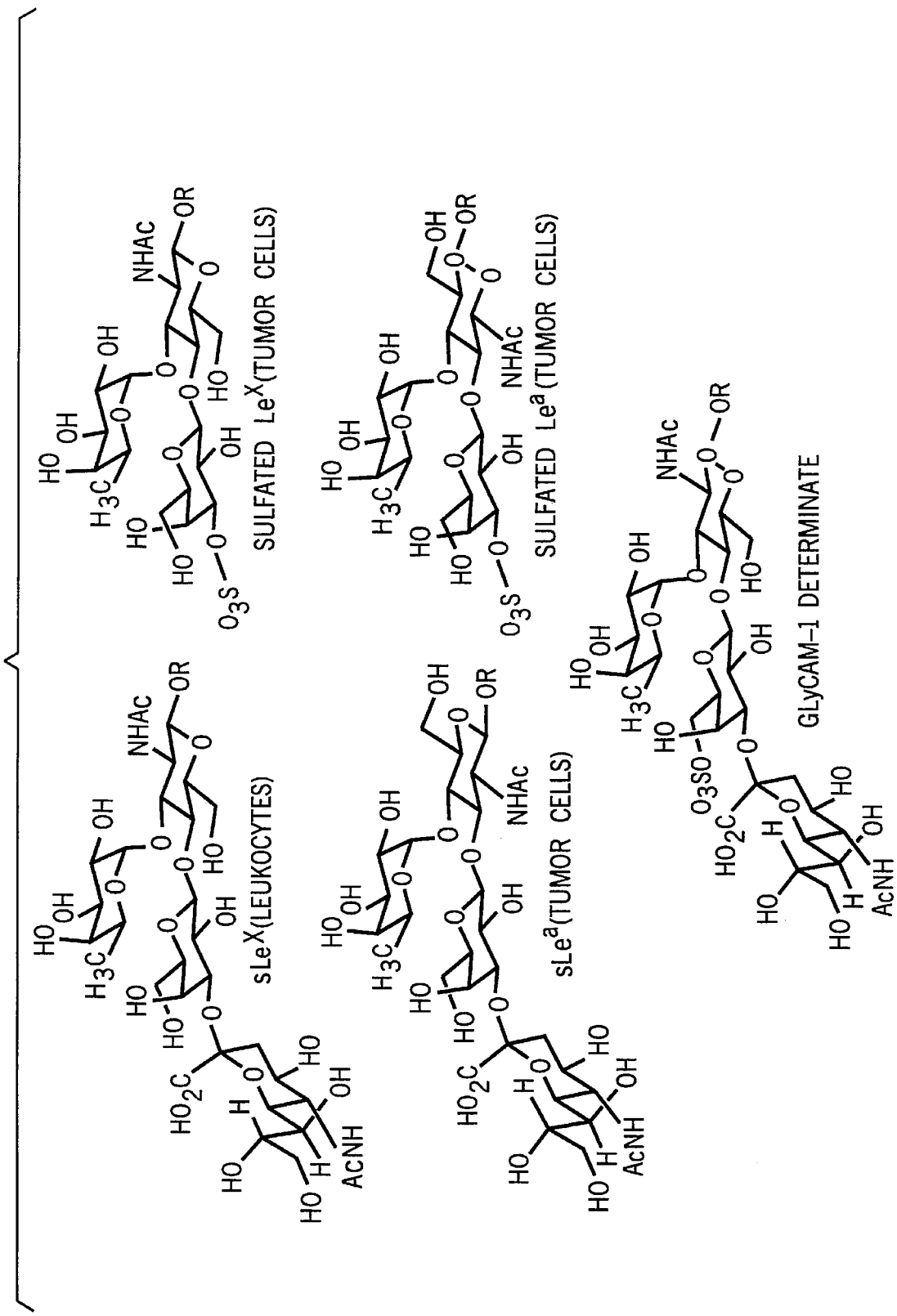
FIG. 4 depicts the naturally occurring low molecular weight oligosaccharides of the Lewis x and Lewis a series that interact with the selectins.

Minimum oligosaccharide determinants that have been shown to interact with the known selectins are sialylated and sulfated derivatives of Lewis a ($Le^a$) and Lewisx($Le^x$) trisaccharides (Varki, *Proc. Natl. Acad. Sci.* 91:7390–7397, 1994). FIG. 4 describes the naturally occurring low molecular weight oligosaccharides of the Lewis x and Lewis a series that interact with the selectins. The sialyl $Le^x$ ($sLe^x$) tetrasaccharide is found in high concentrations on the surface of leukocytes, and sialyl $Le^a$ ($sLe^a$), on cancer cells. Each of the selectins can bind these tetrasaccharides (Foxall, et al., *J. Cell Biol.* 117:895–902, 1992; Berg, et al., *Biochem. Biophys. Res. Commun.* 184:1048–1055, 1992).

In addition to the $sLe^a$ determinant, tumor cells exhibit the $Le^x$ and $Le^a$ sulfates on their surface (Yuen, et al., *Biochemistry* 31:9126–9131, 1992; Berg, et al., *J. Biol. Chem.* 266:14869–14872, 1991), and these derivatives also interact with members of the selectin family.

Solution dissociation constants of these naturally occurring carbohydrate ligands are estimated to be in the 0.1–1 mM range (Welply, et al., *Glycobiology* 4:259–265, 1994; Varki, supra, 1994). The low affinities of the apparent ligands have prompted some to question the biological relevance of the $Le^a$ and $Le^x$ derived ligands (Varki, supra, 1994). Several research teams have detected molecules that bind more avidly (Springer, *Cell* 76:301–314, 1994).

These prior investigations identified high affinity binding glycoproteins for each of the selectins. Two of these, glycoprotein ligands for L- and P-selectin, are mucins (Springer, supra, 1994). The best characterized of these is the L-selectin binding mucin GlyCAM-1, which bears multiple copies of the tetrasaccharide derivative shown in FIG. 4. The identification of mucins as high affinity ligands for the selectins suggests that multivalent interactions could account for the observed high affinity binding.

c. Synthesis of Selectin-targeted Polyglycomers

The Examples below described a detailed synthesis of selectin ligands. These ligands are depicted as oligosaccharides 8, 9 and 10 in FIG. 6. One would use these ligands as described above to produce a selectin-targeted polyglycomer.

We envision that these selectin-targeted compounds will be used for antiflammatory therapeutics. To use such a therapeutic, one would expose the site of inflammation to an effective amount of the polyglycomer. (.See Buerke, et al., *J. Clin. Invest.* 93:1140–1148, 1994 for model of tetrasaccharide delivery.)

EXAMPLES

A. Synthesis and Analysis of Polyglycomers Substituted with Glucose and Fucose

1. In General

The aqueous ring-opening metathesis polymerization (ROMP) has been applied to the synthesis of a new class of carbohydrate substituted polymers. The monomeric precursors were generated by attachment of glucose, fucose or mannose residues to 7-oxanorbornene systems via C-glycoside linkers. Ruthenium catalyzed ROMP of the resulting alkenes affords carbohydrate substituted materials, termed 'polyglycomers'.

The polymers were tested for their ability to function as multivalent ligands for the glucose binding protein concanavalin A (Con A). The multivalent glucose polyglycomer 4 prevented Con A initiated erythrocyte agglutination at a molar glucose concentration 2000-fold lower than that required of the monovalent methyl-α-D-glucopyranoside. The mannose-substituted polymer inhibited agglutination at 20,000-fold lower doses than was required for inhibition by glucose polyglycomer 4.

The application of ROMP to the synthesis of carbohydrate substituted polymers offers new opportunities for the design of materials that can modulate carbohydrateprotein interactions.

2. Synthesis of Polyglycomers a. Materials and Methods

Reaction solvents were freshly distilled from sodiumbenzophenone (tetrahydrofuran), calcium hydride (acetonitrile, dichloromethane, tripropylamine) or magnesium metal (methanol). Chromatography solvents were ACS grade; dichloromethane, acetone and hexanes were distilled. Analytical thin layer chromatography was performed on 0.25 mm Merck precoated silica gel plates (60F-254), and flash chromatography on E. M. Science silica gel-60 (230–400 mesh). $^1H$ and $^{13}C$ NMR spectra were recorded on a Bruker WP-250 or 300 or a Bruker AM-500 Fourier Transform spectrometer. Infrared spectra were obtained on a Mattson Polaris FTIR spectrometer. Mass spectra were obtained on a Kratos MS-80RFA (EI) or a VG AutoSpec M (LSIMS). All reactions were run under an inert atmosphere of either nitrogen or argon. Concanavalin A was obtained from Calbiochem. Other chemicals were obtained from Aldrich and used as supplied. NMR data are reported as: s=singlet, d =doublet, t=triplet, q=quartet, m=multiplet, app=apparent. IR data are reported as: s=strong, m=medium, w=weak.

FIG. 3 describes the reactants necessary to produce fucose-derivatized and glucose-derivatized polyglycomers.

Figure 3A:
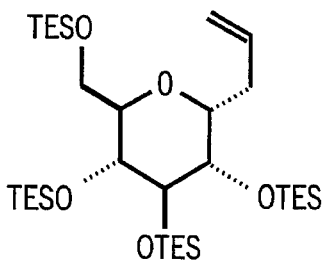
FIGS. 3A through 3F depict the various intermediates and reactants necessary to produce the glucose glycopolymer 4 and the fucose glycopolymer 5.

FIG. 3A depicts 1-C-Allyl-2,3,4,6-tetra-O-triethylsilyl-α-D-glucopyranoside Rf 0.50 (10% ether/hexane). This compound was synthesized by established procedures: β-D-glucose pentaacetate (purchased from Pfanstiehl Laboratories, Waukegan, Ill.) (2.5 g, 1 eq.) is dissolved in dry acetonitrile and cooled to 4° C. under $N_2$. Allyltrimethylsilane (3.5 ml, 3 eq.), freshly distilled borontrifluoride etherate (1.8 ml, 2 eq.) and trimethylsilyl triflate (0.56 ml, 0.4 eq.) are added sequentially. After stirring at 4° C. for 2 hours, followed by 2 hours at 20° C., the reaction is complete by T.L.C. The mixture is cooled to 4° C. and excess acid is quenched with 12 ml of aqueous sodium bicarbonate. The solution was concentrated by rotary evaporation and extracted with 3×75 ml $CH_2Cl_2$. The combined organic phases were dried and evaporated. The residue was purified by flash chromatography to yield a white solid (68%).

The resulting 1-C-allylglucoside is deacylated by reaction with sodium hydroxide (2 mg/ml) in methanol. The residue is filtered through a plug of silica gel. The product (1.2 g, 1 eq.) is dissolved in distilled pyridine (30 ml) with gentle warming and cooled to 4° C. under Ar. Triethylsilyl triflate (11.4 ml, 8 eq.) is added dropwise. After stirring 8 hours at room temperature, the reaction mixture is diluted with ether (200 ml) and the phases are separated. The ether phase is washed with 3×30 ml aqueous ammonium chloride, dried, and evaporated. The residue is purified by flash chromatography to give a clear oil, 1-C-allyl-2,3,4,6-tetra-O-triethylsilyl-α-D-glucopyranoside (91%).

The following describes $^1H$ NMR, $^{13}C$ NMR, IR and HRMS measurements of the FIG. 3A compound:

$^1H$ NMR (500 MHz, $CDCl_3$) δ5.88 (m, 1H, RC$\underline{H}$=$CH_2$), 5.09 (m, 1H, RCH=C$\underline{H}$H'), 5.02 (m, 1H, RCH=CH$\underline{H}$'), 3.84 (dd, J=10.0, 5.5 Hz, 1H, H-6), 3.78 (m, 1H, H-1), 3.73–3.66 (m, 3H, H-2, H-5, H-6'), 3.58 (t, 1H, J=5.0 Hz, H-4), 3.45 (dd, 1H, J=5.0, 3.0 Hz, H-3), 2.43 (m, 1H, Rc$\underline{H}$H'CH=$CH_2$), 2.20 (m, 1H, RCH$\underline{H}$'CH=$CH_2$), 1.04–0.88 (M, 36H, $-SiCH_2C\underline{H}_3$), 0.70–0.52 (m, 24H, $-SiC\underline{H}_2CH_3$).

$^{13}C$ NMR (125 MHz, $CDCl_3$) δ135.7, 116.0, 77.6, 74.0, 71.9, 71.2, 70.4, 62.1, 33.6, 7.01 (broad), 6.96, 6.75, 5.12, 5.07, 4.90, 4.48.

IR (neat film) 1645 $cm_{-1}$ (w), 1459 (m), 1415 (m), 1100 (s), 741 (s).

HRMS (EI) calcd for $C_{31}H_{67}O_5Si_4$ ($M-C_2H_5-$): 331.4066; observed: 331.4003.

Figure 3B:
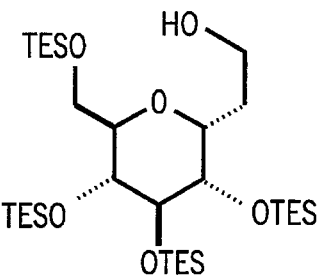

FIG. 3B depicts glucoside alcohol 1. The triethylsilyl protected allyl glucoside described above (0.98 g, 1.48 mmol) was dissolved in a 1:2 mixture of $CH_2Cl_2$/MeOH (12 mL) and cooled to −78° C. Ozone was bubbled through the solution for 6 minutes, until the solution was saturated with ozone. Sodium borohydride (0.6 g, 15 mmol) was added in one portion and the mixture was stirred at −78° C. for 1 hour, then at 3° C. for 1 hour. The reaction was quenched with aqueous ammonium chloride (15 mL), and the mixture was stirred for 1 hour at 3° C. Diethyl ether (20 mL) was added; the aqueous layer was extracted with ether (3×15 mL), and the combined ether extracts were washed with brine, dried over $MgSO_4$, and evaporated. The crude product was purified by flash chromatography (5%–7% ethyl acetate/hexane) to afford a clear oil (0.88 g, 1.33 mmol). Yield: 91%. $R_f$ 0.48 (15% ethyl acetate/hexane).

The following describes $^1H$ NMR, , $^{13}C$ NMR IR and HRMS measurements for the FIG. 3B compound: $^1H$ NMR (500 MHz, $CDCl_3$) δ4.05 (dt, J=10, 2.8 Hz, 1H, H-1), 3.91 (m, 1H, H-6), 3.85 (m, 2H, H-5, RC$\underline{H}$H'OH), 3.77 (m, 1H, RC$\underline{HH}$'OH), 3.71 (t, J=3.5 Hz, 1H, H-3), 3.64 (dd, J=10), 3.5 Hz, 1H, H-6'), 3.45 (dd,J=3.5, 2.8 Hz, 1H, H-2), 3.36 (t, J=3.5 Hz, 1H, H-4), 3.25 (dd, J=7.5, 4.0 Hz, 1H, OH), 2.06 (m, 1H, RC$\underline{H}$H'$CH_2$OH), 1.50 (m, 1H, RCH$\underline{H}$'$CH_2$OH), 1.04–0.88 (m, 36H, $-SiCH_2C\underline{H}_3$), 0.70–0.52 (m, 24H, $-SiC\underline{H}_2CH_3$).

$^{13}C$ NMR (125 MHz, $CDCl_3$) δ77.3, 73.8, 72.2, 70.9, 70.2, 61.5, 61.2, 31.0, 6.95, 6.88 (broad), 6.59, 4.95 (broad), 4.83, 4.22.

IR (neat film) 3600–3170 $cm^{-1}$ (m), 1459 (m), 1415 (m), 1094 (s) 740 (s).

HRMS (EI) calcd for $C_{30}H_{67}O_6Si_4$ ($M-C_2H_5-$): 635.4015; observed: 635.4081.

Figure 3C:
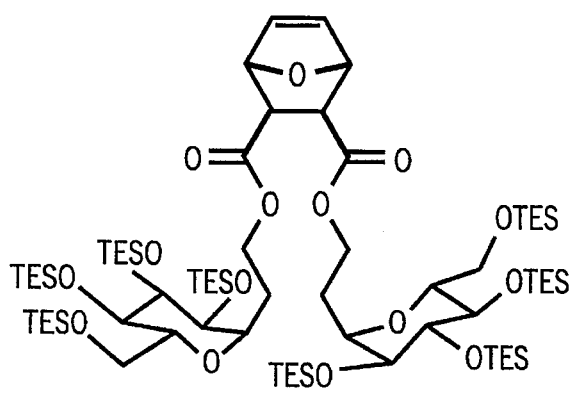

FIG. 3C depicts the precursor to compound 3. Alcohol 1 (0.62 g, 0.94 mmol, 2.5 eq.) was co-distilled with toluene to remove water. 3,6-oxy-1,2,3,6 tetrahydrophthalic anhydride (0.062 g, 0.38 mmol, 1 eq.), 4-dimethylaminopyridine (DMAP, 0.018 g, 0.15 mmol, 0.4 eq.), and 2-chloro-1-methylpyridinium iodide (0.12 g, 0.45 mmol, 1.2 eq.) were added to the alcohol. The flask was filled with argon and $CH_2Cl_2$ (2.0 mL) was added, followed by tripropylamine (0.21 mL, 1.1 mmol, 3 eq.). After stirring at 22° C. overnight, the suspension had cleared to a yellow solution. The reaction was diluted with 20 mL of ether. The ether layer was washed with aqueous ammonium chloride (2×10 mL), and brine (2×10 mL), dried over $MgSO_4$, and evaporated. The residue was purified by flash chromatography (3% ether/toluene) to give a clear oil (0.42 g, 0.27 mmol). Of the excess alcohol added, 82% was recovered. Yield: 72%. Rf 0.57 (15% ethyl acetate/hexane).

The following describes $^1H$ NMR, $^{13}C$ NMR, IR and HRMS measurements for the FIG. 3C compound: $^1H$ NMR (500 MHz, $CDCl_3$) (Resonances for the diastereotopic glucoside residues are superimposed) δ 6.35 (app s, 2H, R$\underline{H}$C=C$\underline{H}$R), 5.13 (app s, 2H, RCHC$\underline{H}$OCHR), 4.30 (m, 2H, $RCO_2C\underline{H}$H'R), 4.18 (m, 2H, $RCO_2$CH$\underline{H}$'R ), 3.87 (m, 4H, H-1, H-6), 3.73–3.62 (m, 8H, H-2, H-3, H-5, H-6"), 3.35 (app dd, J=3.5, 3.0 Hz, 2H, H-4) 2.65 (app s, 2H, C$\underline{H}CO_2R$ ), 1.99 (m, 2H, RC$\underline{H}$H'$CH_2CO_2R$), 1.70 (m, 2H, RCH$\underline{H}$'$CH_2CO_2R$), 1.02–0.91 (m, 72H, $-SiCH_2C\underline{H}_3$), 0.66–0.55 (m, 48H, $-SiC\underline{H}_2CH_3$).

$^{13}C$ NMR (125 MHz, $CDCl_3$) δ 171.1, 136.6, 136.5, 80.6, 77.9, 77.8, 73.83, 73.79, 72.11, 72.08, 69,89, 69.85, 67.5, 67.4, 62.5, 62.4, 62.0, 46.9, 46.7, 28.8, 7.07, 7.03, 6.97, 6.77, 5.02 (broad), 4.83, 4.44.

IR (neat film) 1748 $cm^{-1}$ (m) 1459 (m), 1101 (s) 741 (s).

MS (LSIMS, matrix: 3-NBA+CsI) calcd for $C_{72}H_{147}O_{15}Si_8Cs$ ($M-H+Cs^+$): 1609.8; observed: 1609.9.

Figure 3D:
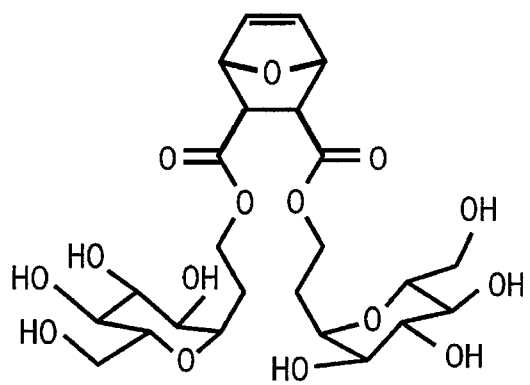

FIG. 3D depicts glucose-substituted monomer 3. The TES-protected precursor to 3 (1.14 g, 772 μmol) was azeotroped with toluene and dissolved in THF (7.5 mL). The resulting solution was cooled in an ice bath. To this solution, HF.pyridine (0.92 mL) was added dropwise. The resulting mixture was stirred at 0° C. for 1.25 hours. The reaction mixture was then concentrated under reduced pressure. Methanol (5 mL) was added to the residue, and solvent was removed under reduced pressure. The residue was purified by flash chromatography (1:4:5 water/methanol/isopropanol eluent) to afford a white solid (0.397 g, 91%). Rf 0.26 (35% MeOH/$CHCl_3$).

The following describes $^1H$ NMR, , $^{13}C$ NMR IR and HRMS measurements for the FIG. 3D compound: $^1H$ NMR (500 MHz, $CD_3OD$) (Resonances for most of the diastereotopic glucoside residues are superimposed) δ 6.48 (app s, 2H, R$\underline{H}$C=C$\underline{H}$R), 5.20 (s, 1H, RCHC$\underline{H}$OCHR), 5.19 (s, 1H, RCHCHOCHR), 4.30–4.12 (m, 4H, RCO$_2$CH$_2$R a,b), 4.07–4.02 (m, 2H, H-1 a,b), 3.79 (d, J=11.6 Hz, 1H, H-6a), 3.78 (d, J=11.6 Hz, 1H, H-6b), 3.66–3.59 (m, 4H, H-2 a,b, 6'a,b), 3.53 (t, J=8.0 Hz, 1H, H-3a), 3.52 (t, J=8.0 Hz, 1H, H-3b), 3.45 (m, 2H, H-5 a,b), 3,26 (t, J=8.0 Hz, 1H, H-4a), 3.25 (t, J=8.0 Hz, 1H, H-4b), 2.88 (app s, 2H, CHCO$_2$R), 2.01–1.99 (m, 4H, RCH$_2$CH$_2$CO$_2$R a,b).

$^{13}$C NMR (125 MHz, CDCl$_3$) δ 173.7, 173.6, 137.7, 137.6, 81.8, 81.7, 75.1, 74.8, 74.7 74.2, 74.1 72.6, 72.2, 72.1, 63.6, 63.5, 63.2, 63.1, 48.0, 25.1, 25.0.

IR (KBr pellet) 3620–2920 cm–1 (s), 1732 (s), 1645 (m), 1083 (s).

HRMS (LSIMS, matrix: 3-NBA) calcd for C$_{24}$H$_{38}$O$_{15}$ (M+H$^+$): 565.2132; observed: 565.2133.

Figure 3E:
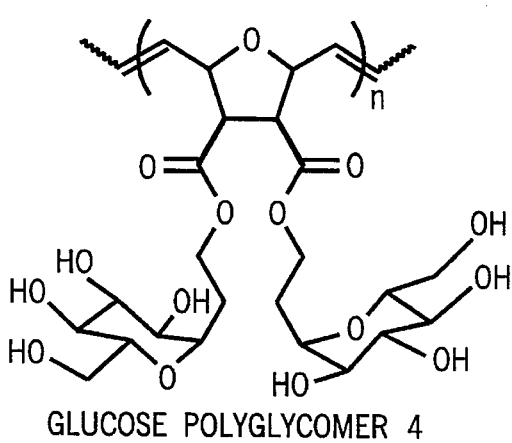
Figure 3F:
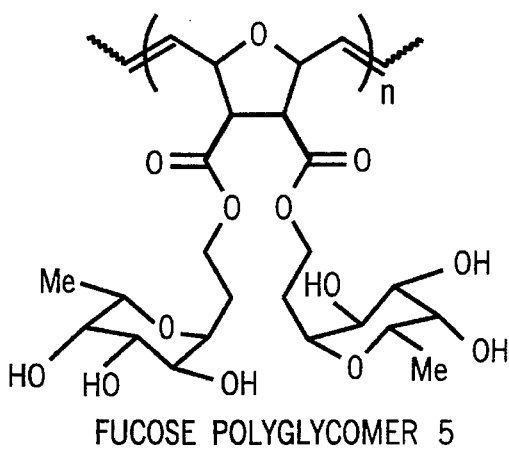

FIG. 3E depicts glucose polyglycomer 4. To a flask containing 7-oxanorbornene 3 (0.132 g, 234 μmol) and RuCl$_3$.H$_2$O (2.0 mg, 9.6 μmol) under N$_2$ was added degassed water. The resulting black solution was heated at 55°–60° C. After 18 hours, a brownish-green gel was obtained, which was washed with acetone (2 mL) and methanol (2 mL) to afford a discolored solid. The solid was dissolved in water (10 mL), concentrated to 2 mL, and precipitated by the addition of methanol (10 mL). The supernatant liquid was decanted and the white precipitate was washed with methanol (2×1 mL). Excess solvent was evaporated under reduced pressure to afford a white solid (0.094 g, 72%).

The following describes $^1$H NMR, $^{13}$C NMR, IR and HRMS measurements for the FIG. 3E compound: $^1$H NMR (500 MHz, DMSO) All peaks are broad. δ 4.71 (s, 0.7H), 4.45 (s, 1.3H), 3.85 (s, 2H), 3.00 (s, 4H), 2.95 (s, 2H), 2.76, 2.31, 2.23, 2.15, 2.02 (m, 14H), 0.77 (s, 4H).

$^{13}$C NMR (125 MHz, DMSO) δ 170.6, 170.4, 132.6–131.7, 73.6, 72.3, 71.1, 70.6, 62.5, 61.4, 52.5, 51.8, 48.7, 23.9.

IR (KBR pellet) 3620–2940 cm$^{-1}$ (s), 1732 (s), 1646 (m), 1083 (s).

FIG. 3F depicts fucose polyglycomer 5. The compound was synthesized by procedures analogous to those detailed for glucose polyglycomer 4 except that the initial reactant was fucose tetraacetate.

The following describes $^1$H NMR, $^{13}$C NMR, IR and HRMS measurements for the FIG. 3F compound: $^1$H NMR (500 MHz, D$_2$O) All peaks are broad. δ 5.92 (s, 1H), 5.70 (s, 1H), 4.91 (s, 2H), 4.18, 4.05, 3.93, 3.85, 3.72 (m, 14H), 3.30 (s, 2H), 2.08 (s, 2H), 1.94 (s, 2H), 1.15 (d, J=4.0 Hz, 6H).

$^{13}$C NMR (125 MHz, D$_2$O) δ 178, 177, 160, 135, 85, 81, 76, 75, 73, 71, 67, 57, 55, 51, 26, 20.

Although not depicted in FIG. 3, a mannose polyglycomer was created by procedures analogous to those described above. Mannose pentaacetate was used in place of glucose pentaacetate as the starting material. All subsequent reactions were identical.

a. Synthesis of Polyglycomers

7-Oxanorbornene derivative 3, designed to produce a polymer with protein binding activity, was synthesized to test whether carbohydrate substituted alkenes will polymerize under aqueous ROMP conditions. FIG. 2 describes the general synthesis strategy. The carbohydrate groups were attached to the oxanorbornene skeleton via C-glycoside linkages. This mode of attachment was chosen for several reasons: (1) the C-glycoside linkage is stable toward chemical and biological assault, (2) the connection at the C1 position of the pyranose ring was designed to allow the glucose residue to interact with the carbohydrate binding protein Con A (Goldstein, In *Concanavalin A as a Tool;* H. Bittiger and H. P. Schnebli, Eds.; John Wiley & Sons, Ltd: London, pp. 55–65, 1976), and (3) C-glycosides of the α-configuration, the preferred anomer for Con A binding, are readily available. (Giannis, et al., *Tetrahedron Lett.* 26:1479–1482, 1985).

Referring to FIG. 2, in the synthesis of monomer 3, two equivalents of alcohol 1 were coupled to anhydride 2 (Diels, et al., *Ber.* 62:554–562, 1929) under modified Mukaiyama esterification conditions as described above and in FIG. 3.

The ROMP of monomer 3 was accomplished by treating with ruthenium trichloride in water (FIG. 3). (Novak, et al., supra, 1988.) The reaction afforded good yields of the carbohydrate substituted polymer 4, which we term a "polyglycomer". This result demonstrates the tolerance of the ruthenium catalyst for highly functionalized monomers, such as 3.

The product polymer 4 was subjected to gel filtration chromatography. By comparison of the migratory aptitude of the polymer relative to dextran standards we estimated that the molecular weight of the polymer was approximately 10$^6$. At a molecular weight of 10$^6$, n=approximately 1800. The mannose and fucose polyglycomers were of a similar size.

The elution profile for a series of molecular weight standards was determined on a 5 cm diameter×70 cm length column packed with Sephacryl SF-1000 gel filtration medium. Samples were run in 0.2M phosphate-buffered saline (pH 7.2) at a flow rate of 0.5 ml/min. A standard curve was generated by plotting the partition coefficient K$_{av}$ versus the log of the molecular weights. Comparison of a polyglycomer K$_{av}$ to the standard curve gives the relative molecular mass. Table 1, below, describes the results.

TABLE 1

| Sample | log MW | elution volume | K$_{av}$ |
|---|---|---|---|
| Reovirus type 3 Dearing (Vo) | 8.0 | 139 | 0 |
| Dextran (2 million) | 6.3 | 218 | 0.35 |
| Dextran (600K) | 5.8 | 325 | 0.83 |
| Dextran (170K) | 5.2 | 364 | 0.97 |
| Phenol Red (Vt) | 2.6 | 70 | 1 |
| Glucose polyglycomer 4 | 6.1 | 254 | 0.51 |
| Fucose polyglycomer 5 | 6.2 | 267 | 0.55 |

The concentration of saccharide moieties present in the polyglycomer solutions were determined by $^1$H NMR and UV spectroscopy. $^1$H NMR spectra of a standard solution of known concentration and of a solution of the fucose polyglycomer 5 were obtained using long recycle delays to ensure complete relaxation (RD=30 sec.). The fucosyl H-6 resonance (δ 1.15 ppm) was integrated and compared to the standard solution integration, giving the fucose residue concentration.

The extinction coefficient (ε) at 210 nm for the fucose polyglycomer solution was calculated: ε$_{210}$=4100 mol$^-$1.cm$^{-1}$. The extinction coefficient for the glucose polyglycomer was assumed to be the same. For the assays, the concentration of a solution of the polyglycomer in pure water was determined by its UV absorbance before adding buffer.

Fucose derivatized polyglycomer 5, synthesized analogously, exhibited the same properties upon analysis by gel filtration.

These water soluble polyglycomers possess unique amphipathic structures with a relatively non-polar polyene backbone and flexible polar side chains. Analysis of $^1$H and $^{13}$C NMR data indicates that the glucose polyglycomer is composed of a 67:33 mixture of Z and E alkenes, and it appears to be atactic.

The $M_r$ of the mannose polyglycomer is also $10^6$. Preliminary analysis of the $^{13}$C NMR data suggests that the mannose polyglycomer is a 48:52 mix of Z and E alkenes and that the polyglycomer appears to be atactic.

3. Analysis of Polyglycomers

The polymers were tested for their ability to function as multivalent ligands for the glucose binding protein Con A. Con A is a well-studied carbohydrate-binding protein, which exists as a homotetramer at neutral pH. Each subunit contains a carbohydrate binding site, and the tetramer can bind simultaneously to four glucose units. The propensity of Con A to agglutinate cells has long been recognized and exploited in biology.

Although the mechanism of cell agglutination is not fully understood, multivalent interactions between Con A and cell surface saccharides are required. (Walther, In *Concanavalin A as a Tool;* H. Bittiger and H. P. Schnebli, Eds.; John Wiley & Sons, Ltd: London, pp. 231–248, 1976; Asahi, et al., *J. Biol. Chem.* 268:23334–23338, 1993; Pestonjamasp, et al., *Biotech. Appl. Biochem.* 12:544–549, 1990.) The requirement for multivalency in Con A activity and the available thermodynamic and structural data make this an ideal model system in which to test polyvalent inhibitors.

To assess the activity of our polymers, we compared the ability of the polymer to inhibit erythrocyte agglutination by Con A with that of several controls including the monovalent carbohydrate derivative methyl-α-D-glucopyranoside and the divalent-glucose substituted 7-oxanorbornene 3.

The agglutination inhibition assays were performed according to standard protocols. (Osawa, et al., *Methods Enzymol.* 28:323–327, 1972.) The assay was as follows: Pure lyophilized Con A was dissolved in HEPES buffer with 100 mM $CaCl_2$, pH 8.0, and dialyzed into phosphate buffered saline (PBS, 25 mM sodium phosphate, 0.15M NaCl), pH 7.2, for the assay. Protein solution concentration was estimated from UV absorbance measurements at 280 nm.

Rabbit red blood cells were stored as a 10% suspension in Alsever's solution and washed 3× with PBS before the assay. For the assay, the cells were pelleted and resuspended in PBS with 0.5% bovine serum albumin.

Polymeric inhibitors were purified by precipitation or by gel filtration. The inhibition results obtained for compounds purified by either method were consistent. The minimum concentration of inhibitor required to inhibit four hemagglutinating doses of Con A was determined. After preincubation with the inhibitor, a 2% suspension of erythrocytes was added. The samples were examined for agglutination after 1 hour at room temperature.

Substrates were incubated with four agglutinating doses of Con A, prior to the addition of rabbit erythrocytes. The concentration of glucose moieties in solution required for inhibition was determined for each substrate within a two-fold dilution.

TABLE 2

| Inhibitor | Inhibiting Dose [carbohydrate residues], M |
|---|---|
| methyl-α-D-glucopyranoside | $5.0 \times 10^{-2}$ |
| 7-oxanorbornene 3 | $2.5 \times 10^{-2}$ |
| glucose polyglycomer 4 | $2.5 \times 10^{-5}$ |
| fucose polyglycomer 5 | $>1.0 \times 10^{-2}$ |

Table 2 describes our results. The glucose polyglycomer prevented erythrocyte agglutination at a glucose moiety concentration at least 2000-fold lower than that required of the monomeric methyl-α-D-glucopyranoside. Inhibiting doses of 7-oxanorbornene 3 were comparable to those of methyl-α-D-glucopyranoside. These data suggest that Con A binds to α-C-glucosides as well as it does to α-O-glucosides, within the limits of our assay. Furthermore, Con A does not bind fucose, (Goldstein, supra, 1976) and the fucose containing polyglycomer 5 showed no inhibition at concentrations up to 10 mM. The inefficacy of the fucose polyglycomer indicates that the strong inhibition exhibited by the glucose polyglycomer is due to binding of glucose residues rather than a non-specific effect of the polymer chain.

Table 3, below, describes the result of a hemagglutination inhibition assay comparing the glucose polyglycomer and the mannose polyglycomer described above. Note that the mannose substituted polymer inhibited agglutination at a 20,000-fold lower dose than was required for inhibition by the glucose polyglycomer.

We had not detected large differences between hemagglutination by glucose and mannose substrates, although calorimetric data indicates that mannose binds to Con A with a slightly higher affinity. However, when the polyglycomers were tested, very different results were obtained. Therefore, we believe that the very small energetic differences in monovalent receptor-ligand complexes are amplified to quite large differences when the interactions are polyvalent. The amplification may lead to tremendous selectivities in the binding of one multivalent ligand over another. These studies indicate that multivalent ligands can exhibit avid and selective binding cell surface targets.

TABLE 3

Hemagglutination Inhibition Assays of Mono- and Multivalent Carbohydrate Derivatives

| Inhibitor | Inhibiting Dose [carbohydrate residues], M |
|---|---|
| methyl-α-D-glucopyranoside | $5.0 \times 0^{-2}$ |
| methyl-α-D-mannopyranoside | $5.0 \times 10^{-2}$ |
| glucose polyglycomer 4 | $2.5 \times 10^{-5}$ |
| mannose polyglcomer | $1.6 \times 10^{-9}$ |

Therefore, we have shown that ROMP can be used to create a polyvalent carbohydrate-bearing polymer that can block protein-initiated cell agglutination. The best natural inhibitors of Con A mediated hemagglutination a. Mandal, et al., *Biochemistry* 32:5117–5120, 1993; b. Mandal, et al., *Biochemistry* 31:12602–12609, 1992), and the glucose polyglycomer share a common feature: multivalency. Progress has been slow in creating high affinity ligands for carbohydrate binding proteins by the traditional approach of modifying the structure of the monovalent ligand. However, imitation of the polyvalent binding environment can create better ligands for the modulation of cellular interactions. As described above, the nature of our polymers allows modifications in the flexibility of the polymer backbone and the structure of the side chains to further optimize biological activity. Additionally, the inclusion of chain-terminating alkenes in the polymerization reaction affords lower molecular weight oligomers, which retain polyvalency with decreased immunogenicity. Thus, the application of ROMP to the synthesis of polyglycomers offers new opportunities for the design of materials for the modulation of cell adhesion, immobilization of particular cell types, and study of multivalency in extracellular interactions.

4. Synthesis of Selectin Ligand a. Monovalent E-, P- and L-Selectin Ligands

Figure 6:
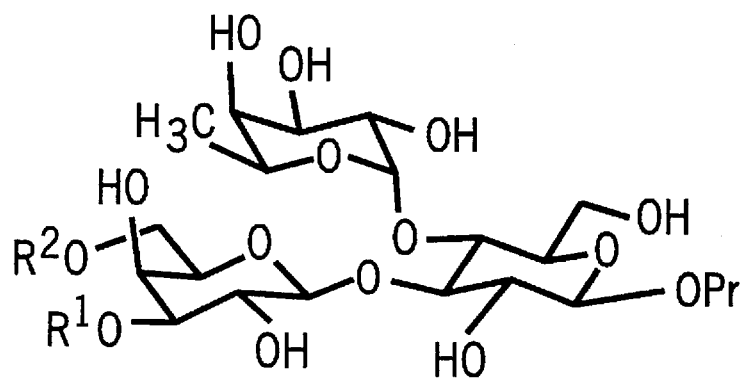
FIG. 6 is a diagram of target molecules 8, 9 and 10 which are designed to act as selectin inhibitors.

Inhibition of selectin requires the attachment of the selectin ligands to various backbones. Consequently, an efficient route to the desired selectin ligands is needed to achieve these aims. We have developed such a route in our synthesis of non-natural oligosaccharides 8, 9 and 10, which are designed to differentially interact with E-, P-, and L-selectin, respectively. FIG. 4 describes the naturally occurring low molecular weight oligosaccharides of the Lewis x and Lewis a series that interact with the selectins. FIG. 6 describes target molecules 8, 9 and 10. Trisaccharide 8 contains the features of the sialylated and sulfated carbohydrates that bind all of the selectins. Trisaccharide 9 is functionalized with a sulfate group at the 6 position of galactose to analyze the effect of an anion at this glyCAM/position. Disulfate 10 possesses the characteristics of the glyCAM1 determinate of the putative L-selectin ligand.

The designs of 8, 9 and 10 are based on the Lewis a rather than Lewis x template, because derivatives of the former generally bind more tightly to the selectins (Berg, et al., *Biochem. Biophys. Res. Commun.* 184:1048–1055, 1992. Nelson, et al., *J. Clin. Invest.* 91:1157–1166, 1993; Yuen, et al., *The J. Biol. Chem.* 269:1595–1598, 1994). To facilitate the syntheses and to simplify structural analyses, sulfate groups in the target molecules have been substituted for sialic acid residues in the naturally occurring saccharides.

Our target selectin inhibitors, sulfates 8, 9 and 10, were generated by chemical synthesis. We chose to employ chemical over enzymatic synthesis because the former provides access to many different carbohydrate derivatives. Although enzymes are available for the generation of Le$^x$ structures, the corresponding Le$^a$ scaffold can not be accessed with currently available glycosyltransferases.

Figure 7:
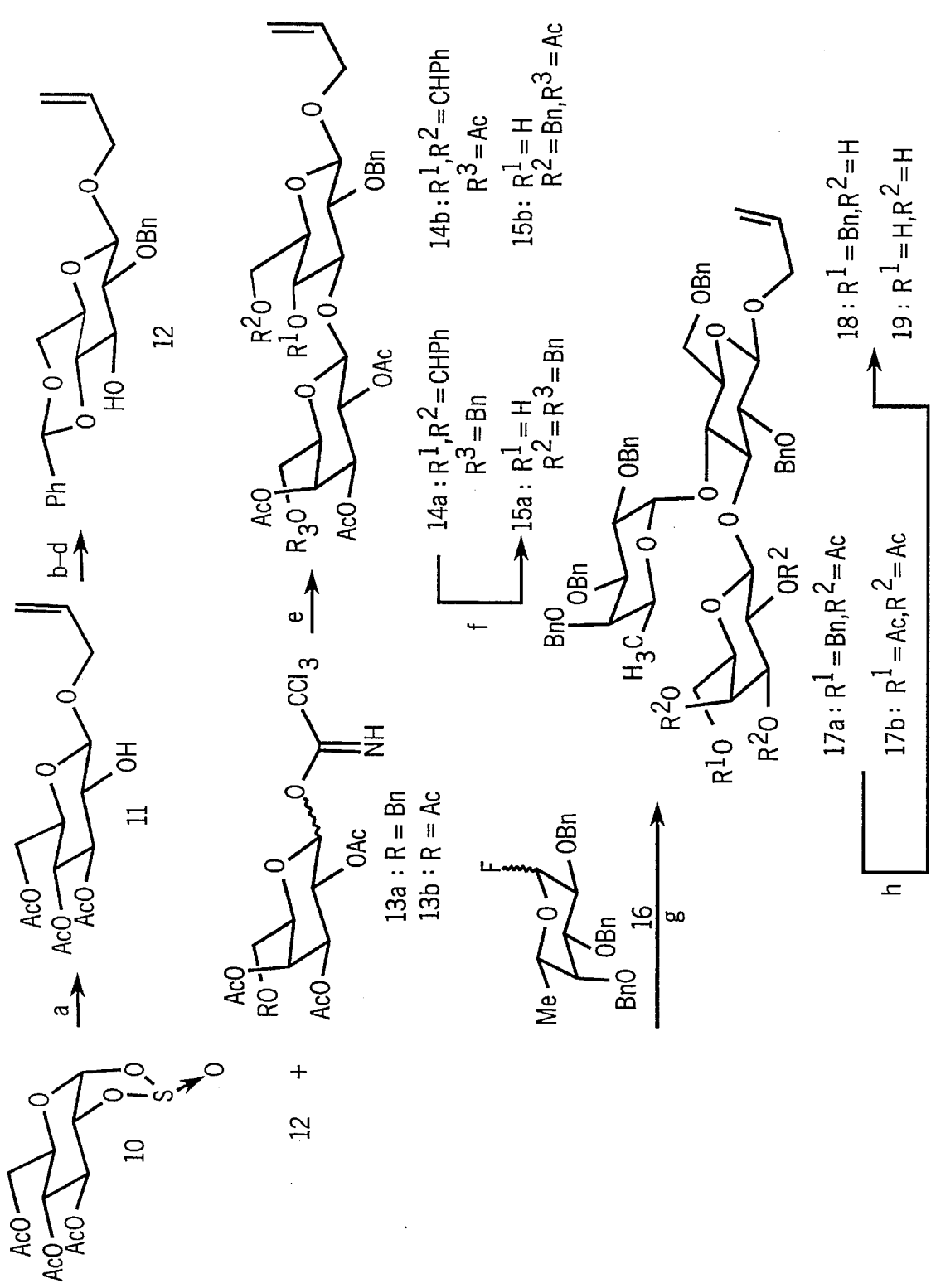
FIG. 7 is a scheme for the synthesis of functionalized Lewis a trisaccharide templates 18 and 19.
Figure 8:
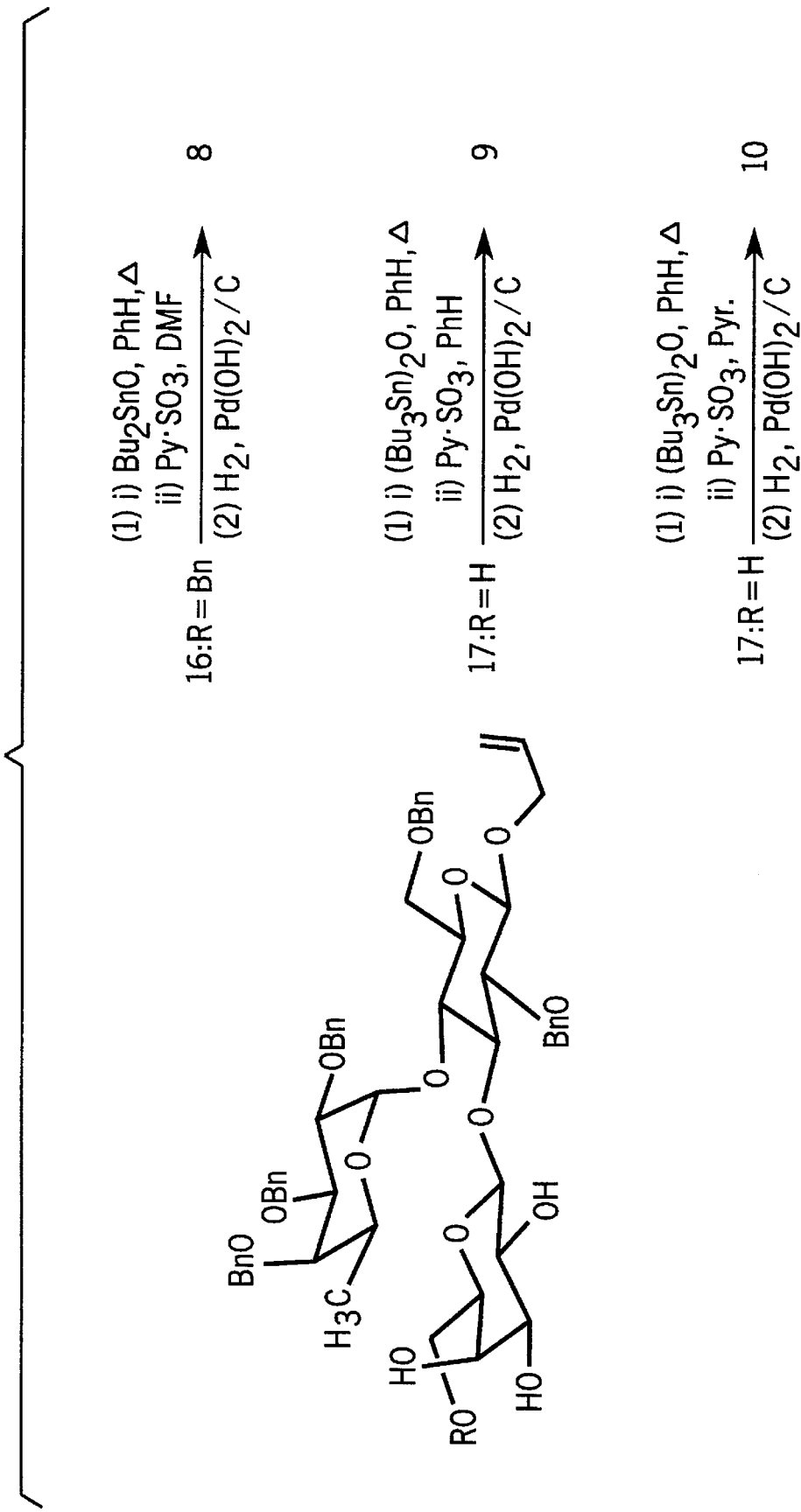
FIG. 8 depicts the selective sulfation of Lewis a trisaccharides to afford selectin ligands 8, 9 and 10.

With these considerations in mind, we developed routes to trisaccharides 8, 9 and 10, which employ selective sulfation reactions of lightly protected carbohydrates to produce the desired compounds (FIGS. 7 and 8). An important criterion in the design of our route was that it should allow the attachment of the final product (or a precursor) to a template so that a polyglycomer can be produced. The allyl protecting group utilized serves two functions: it allows subsequent derivatization for coupling of the trisaccharide to a oxanorbornene or peptide template, and it anchors the anomeric configuration at the reducing end of the trisaccharide, facilitating structural determination.

Compounds 8, 9 and 10 were synthesized in twelve linear steps and in 18% overall yield by a route that meets our requirement for efficiency (FIGS. 7 and 8). Referring to FIGS. 7 and 8, reagents and conditions are: (a) cat. Yb(OTf)$_3$, 3 Å mol sieves, allyl alcohol, toluene, 100° C., 82%; (b) benzyltrichloroacetimidate, cyclohexane, TMSOTf, 97%; (c) K$_2$CO$_3$, MeOH; (d) p-TsOH, DMF, benzaldehyde dimethylacetal, 50° C., reduced pressure, 77% (2 steps); (e) 1.1 eq 13a, 0.1M TMSOTf, CH$_2$Cl$_2$, 85%; 1.1 eq 13b, 0.01M TMSOTf, CH$_2$Cl$_2$, 87%; (f) 14a: (i) 4 eq NaCNBH$_3$, THF 3 Å mol sieves, (ii) cold saturated Et$_2$O.HCl, 72%; 14b: 5 eq Et$_3$SiH, 5 eq TFA, 0° C., 77%; (g) 15a: 2.8 eq of 16, 1.6 eq Bu$_2$SnCl$_2$, 3.1 eq AgOTf, 1.5 eq 2,6-di-tertbutyl-4-methylpyridine, 4 Å mol sieves, toluene, 0° C., 90%; 15b: 2.5 eq of 5, 1.5 eq Bu$_2$SnCl$_2$, 3.1 eq AgOTf, 1.5 eq 2,6-di-tertbutyl-4-methylpyridine, 4 Å mol sieves, toluene, 0° C., 90%; (h) 17a: K$_2$CO$_3$, 1:1 MeOH: THF, (86%); 17b: K$_2$CO$_3$, MeOH, 91%.

The differentially protected glucose residue 12 was generated from cyclic sulfite 10 using a glycosylation method developed in our laboratory (Sanders, et al., *Tetrahedron Lett.* 35, 7334, 1994). The fucose residue 16 and the galactose partners 13a and 13b are available through standard manipulations (Manning, et al., 1994, in preparation, supplemental material). The glycosylations to form lactose derivatives 14a and 14b were promoted with Schmidt glycosylation conditions (Schmidt, In *Comprehensive Organic Synthesis*; B. M. Trost and I. Fleming, Eds.; Pergamon Press: New York, N.Y., pp. 33–64, 1991; Schmidt, et al., *Tetrahedron Lett.* 32:3353–3356, 1991). Attachment of the fucose residue to generate 17a and 17b was achieved with a modified Suzuki coupling protocol (Maeta, *Carbohydrate Res.* 249:49–56, 1993). The stereochemical outcome of this glycosylation reaction was dramatically altered by solvent, with toluene affording the stereochemically desired Q-linkage in high selectivity. To obtain the desired sulfate regioisomers from triol 18 and tetraol 19, tin acetal chemistry was employed (FIG. 8).

Compound 8 was sulfated by way of the cyclic tin acetal, which forms at the 3 and 4 hydroxyls of the galactose residue. The disulfate was selectively generated through the intermediate wherein regioselective tin complexation occurred at the 6 and the 3 positions of galactose. The positions of sulfation were unambiguously identified through complete assignments of the $^1$H and $^{13}$C coupling constants and chemical shifts.

The structures of 8, 9 and 10 were determined through a combination of two dimensional NMR experiments including DQF-COSY (homonuclear shift correlation), HMQC (heteronuclear correlation through multiple quantum coherence), TOCSY (total correlation spectroscopy), and HMBC (long range heteronuclear shift correlation).

b. ELISA assay of compounds 8, 9 and 10

The affinity of compounds 8, 9 and 10 for each selectin were tested in an ELISA assay that compares their ability to inhibit binding of the selectins to immobilized GlyCAM-1. Because all of the selectins bind to GlyCAM-1 (FIG. 4) this assay provides insight into the relative affinities and specificities of the identified GlyCAM-1 component for each selectin.

The ELISAs were executed by the following protocol: An antibody to GlyCAM-1 was immobilized in a microtiter well. GlyCAM-1 was added. Selectin-IgG chimeras, which were biotinylated, were added to streptavidin-alkaline phosphatase conjugate. The binding of the selectin-IgGbiotin •strepavidin-alkaline phosphatase to GlyCAM-1 was monitored by UV. Para-nitrophenolate is produced from alkaline phosphatase catalyzed hydrolysis of paranitrophenolphosphate (Qed). The inhibitory effects of saccharides 8–10 on selectin-IgG binding to immobilized GlyCAM-1 were measured by this method.

The relative abilities of compounds 8, 9 and 10 to block binding of L-, E- and P-selectin to immobilized GlyCAM-1 were then assayed. All three Le$^a$ sulfates were comparably effective at preventing L-selectin binding with IC$_{50}$s in the mmolar range. The 3,6-disulfo compound 10 thought to mimic the GlyCAM-1 determinant bound no more tightly to L-selectin than the 3- and 6-sulfo analogs 8 and 9. The three compounds did show differential binding in an unexpected manner to E- and P-selectin. The 3-sulfo derivative 8 was considerably more effective than the 6-sulfate 9 or the 3,6-disulfate 10 in binding to E-selectin. However, with P-selectin the 3-monosulfate 8 was the worst at blocking binding, the 6-sulfo derivative 9 slightly better, and the 3,6-disulfate 10 the most active.

c. Synthesis of Polyglycomer

With the ligands 8, 9 and 10 in hand, the synthesis of multivalent selectin ligands can be envisioned through conjugation of trisaccharides 8, 9 and 10 to various scaffolds.

Figure 12:
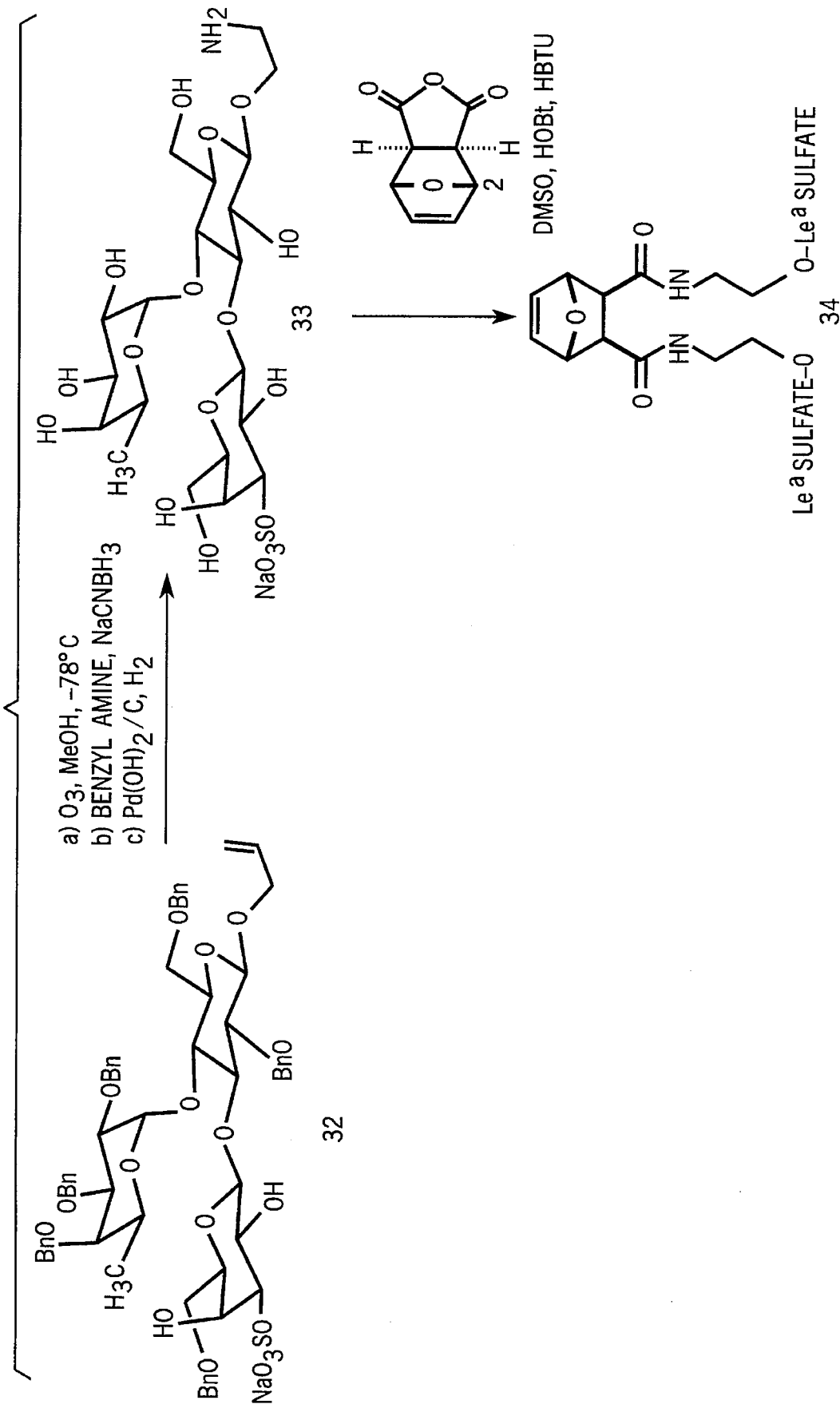
FIG. 12 describes a proposed synthesis of compound 34.

FIG. 12 describes our envisioned synthesis of a selectin-targeted polyglycomer. 34 will be polymerized according to the conditions previously developed (i.e. RuCl$_3$H$_2$O or Ruthenium tosylate).

We claim:

1. A polyglycomer of the formula

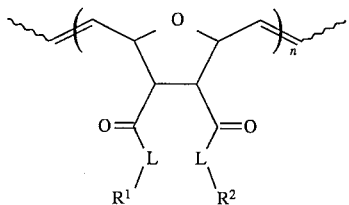

wherein L is a linker selected from the group of —O—(CH$_2$)$_m$—, —NH—(CH$_2$)$_m$—, —O—(CH$_2$)$_m$—X—, and —NH—(CH$_2$)$_m$—X—, wherein X is S or O and m is 2–10, wherein R$^1$ and R$^2$ are selected from the group consisting of monosaccharides, disaccharides, trisaccharides, and oligosaccharides, and wherein n is between 1 and 2000.

2. The polyglycomer of claim 1 wherein R$^1$ and R$^2$ are hexoses.

3. The polyglycomer of claim 1 wherein R$^1$ and R$^2$ are not the same saccharide.

4. The polyglycomer of claim 1 wherein L is —O—CH$_2$—CH$_2$—.

5. The polyglycomer of claim 1 wherein R$^1$ and R$^2$ are selected from the group of glucose, fucose and mannose.

6. The polyglycomer of claim 1 wherein n is between 1000 and 2000.

7. The polyglycomer of claim 1 wherein n is less than 20.

8. The polyglycomer of claim 1 wherein n is between 500 and 1800.

9. The polyglycomer of claim 1 wherein the saccharide moieties are sulfated.

10. A polyglycomer of the formula

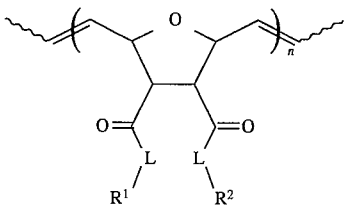

wherein L is a linker selected from the group of —O—(CH$_2$)$_m$—, —NH—(CH$_2$)$_m$—, —O—(CH$_2$)$_m$—X—, and —NH—(CH$_2$)$_m$—X—, wherein X is S or O and m is 2–10, wherein R$^1$ and R$^2$ are selected from the group consisting of moieties of the formula

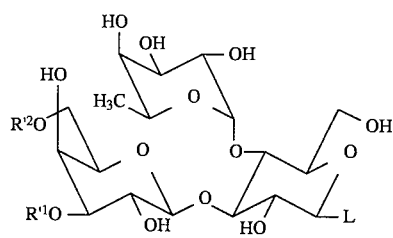

wherein R'$^1$=SO$_3$Na and R'$^2$=H; or R'$^1$=SO$_3$Na and R'$^2$=SO$_3$Na; or R'$^1$=H and R'$^2$=SO$_3$Na, and wherein n is between 1 and 2000.

11. A polyglycomer of the formula

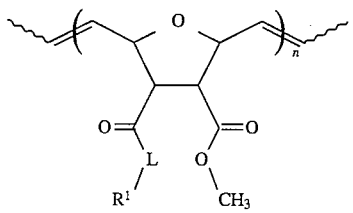

wherein L is a linker selected from the group of —O—(CH$_2$)$_m$—, —NH—(CH$_2$)$_m$—, —O—(CH$_2$)$_m$—X—, and —NH—(CH$_2$)$_m$—X—, wherein X is S or O and m is 2–10, wherein R$^1$ is selected from the group consisting of saccharide moieties, and wherein n is between 1 and 2000.

12. A polyglycomer of the formula

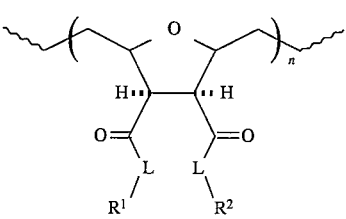

wherein L is a linker selected from the group of —O—(CH$_2$)$_m$—, —NH—(CH$_2$)$_m$—, —O—(CH$_2$)$_m$—X—, and —NH—(CH$_2$)$_m$—X—, wherein X is S or O and m is 2–10, wherein R$^1$ and R$^2$ are selected from the group consisting of saccharide moieties, and wherein n is between 1 and 2000.

13. A method of synthesizing a polyglycomer comprising the steps of:

(1) attaching at least one saccharide group to 7-oxanorbornene via a C-glycoside linkage; and (2) treating the product of step (1) with ruthenium catalyst, wherein a polyglycomer is synthesized.

14. A polyglycomer produced by the method of claim 13.

15. A method of treating inflammation in a human patient comprising applying an effective amount of a polyglycomer of the formula

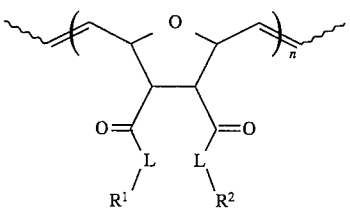

wherein L is a linker selected from the group of —O—(CH$_2$)$_m$—, —NH—(CH$_2$)$_m$—, —O—(CH$_2$)$_m$—X—, and —NH—(CH$_2$)$_m$—X—, wherein X is S or O and m is 2–10, wherein R$^1$ and R$^2$ are selected from the group consisting of sulfated monosaccharides, disaccharides, trisaccharides, and oligosaccharides, wherein the application is intravenous, and wherein n is between 1 and 2000.

16. A polyglycomer of the formula
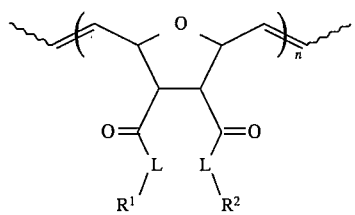
wherein L is a linker selected from the group of $-O-(CH_2)_m-$, $-NH-(CH_2)_m-$, $-O-(CH_2)_m-X-$, and $-NH-(CH_2)_m-X-$, wherein X is S or O and m is 2–10,
wherein $R^1$ and $R^2$ are ligands, and
wherein n is between 1 and 2000.
* * * * *